Figure 1:
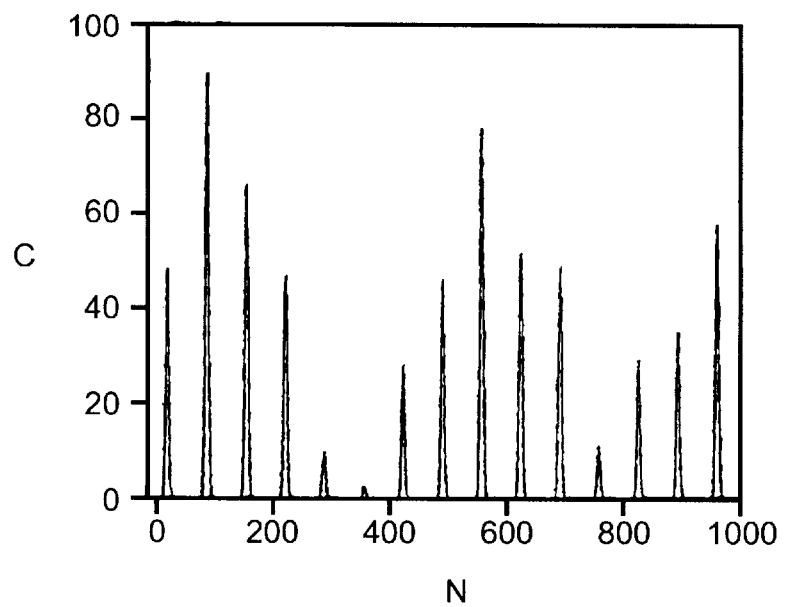

United States Patent [19]

Warren et al.

[11] Patent Number: 5,814,473
[45] Date of Patent: Sep. 29, 1998

[54] TRANSAMINASES AND AMINOTRANSFERASES

[75] Inventors: Patrick V. Warren, Philadelphia; Ronald V. Swanson, Media, both of Pa.

[73] Assignee: Diversa Corporation, La Jolla, Calif.

[21] Appl. No.: 599,171

[22] Filed: Feb. 9, 1996

[51] Int. Cl.⁶ .............................. C12Q 1/48; C12Q 1/52; C12P 21/06; C12N 9/10
[52] U.S. Cl. .................. 435/15; 435/16; 435/69.01; 435/70.1; 435/193; 435/252.3; 435/320.1; 435/128; 536/23.2
[58] Field of Search ................... 435/69.1, 70.1, 435/193, 252.3, 320.1, 15, 16, 128; 536/23.2

[56] References Cited

PUBLICATIONS

Wetmur et al., "Cloning, sequencing, and expression of RecA proteins from three distantly related Thermophlilic eubacteria,"*J. Biol. Chem.* Oct. 14, 1994, vol. 269, No. 41, pp. 25928–25935.

Brown et al., "Root of the universal tree of life based on ancient aminoacyl–tRNA synthetase gene duplications," *Proc. Natl. Acad. Sci.,* USA Mar., 1995, vol. 92, No. 7, pp. 2441–2445.

Volkl et al., "Genomic and cDNA sequence tags of the hyperthermophilic archeon *Pyrobaculum aerophilum,*" *Nucleic Acids Res.* 1996, vol. 24, No. 22, pp. 4373–4378.

*Primary Examiner*—Robert A. Wax
*Assistant Examiner*—Elizabeth Slobodyansky
*Attorney, Agent, or Firm*—Fish & Richardson, P.C.

[57] ABSTRACT

Thermostable transaminase and aminotransferase enzymes derived from various *ammonifex, aquifex* and *pyrobaculum* organisms are disclosed. The enzymes are produced from native or recombinant host cells and can be utilized in the pharmaceutical, agricultural and other industries.

16 Claims, 1 Drawing Sheet

5,814,473

TRANSAMINASES AND AMINOTRANSFERASES

This invention relates to newly identified polynucleotides, polypeptides encoded by such polynucleotides, the use of such polynucleotides and polypeptides, as well as the production and isolation of such polynucleotides and polypeptides. More particularly, the polynucleotides and polypeptides of the present invention have been putatively identified as transaminases and/or aminotransferases. Aminotransferases are enzymes that catalyze the transfer of amino groups from α-amino to α-keto acids. They are also called transaminases.

The α-amino groups of the 20 L-amino acids commonly found in proteins are removed during the oxidative degradation of the amino acids. The removal of the α-amino groups, the first step in the catabolism of most of the L-amino acids, is promoted by aminotransferases (or transaminases). In these transamination reactions, the α-amino group is transferred to the α-carbon atom of α-ketoglutarate, leaving behind the corresponding α-keto acid analog of the amino acid. There is no net deamination (i.e., loss of amino groups) in such reactions because the α-ketoglutarate becomes aminated as the α-amino acid is deaminated. The effect of transamination reactions is to collect the amino groups from many different amino acids in the form of only one, namely, L-glutamate. The glutamate channels amino groups either into biosynthetic pathways or into a final sequence of reactions by which nitrogenous waste products are formed and then excreted.

Cells contain several different aminotransferases, many specific for α-ketoglutarate as the amino group acceptor. The aminotransferases differ in their specificity for the other substrate, the L-amino acid that donates the amino group, and are named for the amino group donor. The reactions catalyzed by the aminotransferases are freely reversible, having an equilibrium constant of about 1.0 ($\Delta G^{0'} \cong 0$ kJ/mol).

Aminotransferases are classic examples of enzymes catalyzing bimolecular ping-pong reactions. In such reactions the first substrate must leave the active site before the second substrate can bind. Thus the incoming amino acid binds to the active site, donates its amino group to pyridoxal phosphate, and departs in the form of an α-keto acid. Then the incoming α-keto acid is bound, accepts the amino group from pyridoxamine phosphate, and departs in the form of an amino acid.

The measurement of alanine aminotransferase and aspartate aminotransferase levels in blood serum is an important diagnostic procedure in medicine, used as an indicator of heart damage and to monitor recovery from the damage.

The polynucleotides and polypeptides of the present invention have been identified as transaminases and/or aminotransferases as a result of their enzymatic activity.

In accordance with one aspect of the present invention, there are provided novel enzymes, as well as active fragments, analogs and derivatives thereof.

In accordance with another aspect of the present invention, there are provided isolated nucleic acid molecules encoding the enzymes of the present invention including mRNAs, cDNAs, genomic DNAs as well as active analogs and fragments of such enzymes.

In accordance with yet a further aspect of the present invention, there is provided a process for producing such polypeptides by recombinant techniques comprising culturing recombinant prokaryotic and/or eukaryotic host cells, containing a nucleic acid sequence of the present invention, under conditions promoting expression of said enzymes and subsequent recovery of said enzymes.

In accordance with yet a further aspect of the present invention, there is provided a process for utilizing such enzymes, or polynucleotides encoding such enzymes for transferring an amino group from an a-amino acid to an a-keto acid. Most transaminases use L-amino acids as substrates, but as described below, it is also possible to convert the transaminases of the invention to use D-amino acids as substrates, thereby increasing their array of uses to include, for example, manufacture of synthetic pyrethroids and as components of β-lactam antibiotics. The transaminases of the invention are stable at high temperatures and in organic solvents and, thus, are superior for use with L- and/or D-amino acids for production of optically pure chiral compounds used in pharmaceutical, agricultural and other chemical industries.

In accordance with yet a further aspect of the present invention, there are also provided nucleic acid probes comprising nucleic acid molecules of sufficient length to hybridize to a nucleic acid sequence of the present invention.

In accordance with yet a further aspect of the present invention, there is provided a process for utilizing such enzymes, or polynucleotides encoding such enzymes, for in vitro purposes related to scientific research, for example, to generate probes for identifying similar sequences which might encode similar enzymes from other organisms by using certain regions, i.e., conserved sequence regions, of the nucleotide sequence.

The following drawings are illustrative of embodiments of the invention and are not meant to limit the scope of the invention as encompassed by the claims.

FIG. 1 is a diagramatic illustration of the assay used to assess aminotransferase activity of the proteins using glutamate dehydrogenase.

The term "gene" means the segment of DNA involved in producing a polypeptide chain; it includes regions preceding and following the coding region (leader and trailer) as well as intervening sequences (introns) between individual coding segments (exons).

A coding sequence is "operably linked to" another coding sequence when RNA polymerase will transcribe the two coding sequences into a single mRNA, which is then translated into a single polypeptide having amino acids derived from both coding sequences. The coding sequences need not be contiguous to one another so long as the expressed sequences ultimately process to produce the desired protein.

"Recombinant" enzymes refer to enzymes produced by recombinant DNA techniques; i.e., produced from cells transformed by an exogenous DNA construct encoding the desired enzyme. "Synthetic" enzymes are those prepared by chemical synthesis.

A DNA "coding sequence of" or a "nucleotide sequence encoding" a particular enzyme, is a DNA sequence which is transcribed and translated into an enzyme when placed under the control of appropriate regulatory sequences.

In accordance with an aspect of the present invention, there are provided isolated nucleic acids (polynucleotides) which encode for the mature enzymes having the deduced amino acid sequences of FIGS. 1–8 (SEQ ID NOS: 17–32).

The deposit(s) have been made under the terms of the Budapest Treaty on the International Recognition of the deposit of micro-organisms for purposes of patent procedure. The strains will be irrevocably and without restriction or condition released to the public upon the issuance of a patent. These deposits are provided merely as convenience to those of skill in the art and are not an admission that a deposit would be required under 35 U.S.C. §112. The sequences of the polynucleotides contained in the deposited materials, as well as the amino acid sequences of the polypeptides encoded thereby, are controlling in the event of any conflict with any description of sequences herein. A license may be required to make, use or sell the deposited materials, and no such license is hereby granted.

The polynucleotides of this invention were originally recovered from genomic DNA libraries derived from the following organisms:

*Aquifex* VF5 is a Eubacteria which was isolated in Vulcano, Italy. It is a gram-negative, rod-shaped, strictly chemolithoautotrophic, marine organism which grows optimally at 85°–90° C. ($T_{max}$=95° C.) at pH 6.8 in a high salt culture medium with $O_2$ as a substrate, and $H_2/CO_2$+0.5% $O_2$ in gas phase.

*Ammonifex degensii* KC4 is a new Eubacaterial organism isolated in Java, Indonesia. This Gram negative chemolithoautotroph has three respiration systems. The bacterium can utilize nitrate, sulfate, and sulfur. The organism grows optimally at 70° C., and pH 7.0, in a low salt culture medium with 0.2% nitrate as a substrate and $H_2/CO_2$ in gas phase.

*Pyrobaculum aerophilium* IM2 is a thermophilic sulfur archaea (Crenarchaeota) isolated in Ischia Maronti, Italy. It is a rod-shaped organism that grows optimally at 100° C. at pH 7.0 in a low salt culture medium with nitrate, yeast extract, peptone, and $O_2$ as substrates and $N_2/CO_2$, $O_2$ in gas phase.

Accordingly, the polynucleotides and enzymes encoded thereby are identified by the organism from which they were isolated, and are sometimes hereinafter referred to as "VF5/ATA" (SEQ ID NOS: 17 and 25), "VF5/AAB" (SEQ ID NOS: 18 and 26), "VF5/A87A" (SEQ ID NOS: 19 and 27), "VF5/AOA" (SEQ ID NOS:20 and 28), "KC4/AA" (SEQ ID NOS:21 and 29), "VF5/GF6PA" (SEQ ID NOS:22 and 30), "VF5/HPA" (SEQ ID NOS:23 and 31) and "IM2/BCA" (SEQ ID NOS:24 and 32).

The polynucleotides and polypeptides of the present invention show identity at the nucleotide and protein level to known genes and proteins encoded thereby as shown in Table 1.

TABLE 1

| Enzyme | Gene w/closest Homology (Organism) | Protein Similarity (%) | Protein Identity (%) | DNA Identity (%) |
|---|---|---|---|---|
| VF5/ATA | *Bacillus subtilis* | 57.5 | 38.3 | 50.1 |
| VF5/AAB | *Sulfolobus solfataricus* | 62.5 | 33.0 | 50.1 |
| VF5/A87A | *Bacillus sphaericus* BioA | 67.4 | 42.9 | 51 |
| VF5/AOA | *Bacillus subtilis* argD | 70.6 | 48.7 | 52.0 |
| KC4/AA | Bacillus YM-2 aspC | 72.6 | 52.7 | 52.0 |
| VF5/GF6PA | *Rhizobium Leguminosarum* NodM | 66.3 | 47.7 | 51.0 |
| VF5/HPA | *Bacillus subtilis* HisH/*E. coli* HisC (same gene) | 55.7 | 32.6 | 45.3 |
| IM2/BCA | *E. coli* iluE | 63.7 | 43.6 | 49.7 |

All the clones identified in Table 1 encode polypeptides which have transaminase or aminotransferase activity.

One means for isolating the nucleic acid molecules encoding the enzymes of the present invention is to probe a gene library with a natural or artificially designed probe using art recognized procedures (see, for example: Current Protocols in Molecular Biology, Ausubel F. M. et al. (EDS.) Green Publishing Company Assoc. and John Wiley Interscience, New York, 1989, 1992). It is appreciated by one skilled in the art that the polynucleotides of SEQ ID NOS:17–24, or fragments thereof (comprising at least 12 contiguous nucleotides), are particularly useful probes. Other particularly useful probes for this purpose are hybridizable fragments of the sequences of SEQ ID NOS: 1–9 (i.e., comprising at least 12 contiguous nucleotides).

With respect to nucleic acid sequences which hybridize to specific nucleic acid sequences disclosed herein, hybridization may be carried out under conditions of reduced stringency, medium stringency or even stringent conditions. As an example of oligonucleotide hybridization, a polymer membrane containing immobilized denatured nucleic acids is first prehybridized for 30 minutes at 45° C. in a solution consisting of 0.9 M NaCl, 50 mM $NaH_2PO_4$, pH 7.0, 5.0 mM $Na_2EDTA$, 0.5% SDS, 10X Denhardt's, and 0.5 mg/mL polyriboadenylic acid. Approximately $2\times10^7$ cpm (specific activity $4-9\times10^8$ cpm/ug) of $^{32}$p end-labeled oligonucleotide probe are then added to the solution. After 12–16 hours of incubation, the membrane is washed for 30 minutes at room temperature in 1X SET (150 mM NaCl, 20 mM Tris hydrochloride, pH 7.8, 1 mM $Na_2EDTA$) containing 0.5% SDS, followed by a 30 minute wash in fresh 1X SET at Tm −10° C. (Tm is minus 10° C.) for the oligo-nucleotide probe. The membrane is then exposed to auto-radiographic film for detection of hybridization signals.

Stringent conditions means hybridization will occur only if there is at least 90% identity, preferably at least 95% identity and most preferably at least 97% identity between the sequences. See J. Sambrook et al., *Molecular Cloning, A Laboratory Manual, 2d Ed.*, Cold Spring Harbor Laboratory (1989) which is hereby incorporated by reference in its entirety.

As used herein, a first DNA (RNA) sequence is at least 70% and preferably at least 80% identical to another DNA (RNA) sequence if there is at least 70% and preferably at least a 80% or 90% identity, respectively, between the bases of the first sequence and the bases of the another sequence, when properly aligned with each other, for example when aligned by BLASTN.

The present invention relates to polynucleotides which differ from the reference polynucleotide such that the changes are silent changes, for example the change does not or the changes do not alter the amino acid sequence encoded by the polynucleotide. The present invention also relates to nucleotide changes which result in amino acid substitutions, additions, deletions, fusions and truncations in the polypeptide encoded by the reference polynucleotide. In a preferred aspect of the invention these polypeptides retain the same biological action as the polypeptide encoded by the reference polynucleotide.

The polynucleotides of this invention were recovered from genomic gene libraries from the organisms listed in Table 1. Gene libraries were generated in the Lambda ZAP II cloning vector (Stratagene Cloning Systems). Mass excisions were performed on these libraries to generate libraries in the pBluescript phagemid. Libraries were generated and excisions were performed according to the protocols/methods hereinafter described.

The polynucleotides of the present invention may be in the form of RNA or DNA which DNA includes cDNA, genomic DNA, and synthetic DNA. The DNA may be double-stranded or single-stranded, and if single stranded may be the coding strand or non-coding (anti-sense) strand. The coding sequences which encodes the mature enzymes may be identical to the coding sequences shown in SEQ ID NOS: 17–24 or may be a different coding sequence which coding sequence, as a result of the redundancy or degeneracy of the genetic code, encodes the same mature enzymes as the DNA of SEQ ID NOS:17–24.

The polynucleotide which encodes for the mature enzyme of SEQ ID NOS:25–32 may include, but is not limited to: only the coding sequence for the mature enzyme; the coding sequence for the mature enzyme and additional coding sequence such as a leader sequence or a proprotein sequence; the coding sequence for the mature enzyme (and optionally additional coding sequence) and non-coding sequence, such as introns or non-coding sequence 5' and/or 3' of the coding sequence for the mature enzyme.

Thus, the term "polynucleotide encoding an enzyme (protein)" encompasses a polynucleotide which includes only coding sequence for the enzyme as well as a polynucleotide which includes additional coding and/or non-coding sequence.

The present invention further relates to variants of the hereinabove described polynucleotides which encode for fragments, analogs and derivatives of the enzymes having the deduced amino acid sequences of SEQ ID NOS:25–32. The variant of the polynucleotide may be a naturally occurring allelic variant of the polynucleotide or a non-naturally occurring variant of the polynucleotide.

Thus, the present invention includes polynucleotides encoding the same mature enzymes as shown in SEQ ID NOS:17–24 as well as variants of such polynucleotides which variants encode for a fragment, derivative or analog of the enzymes of SEQ ID NOS: 17–24. Such nucleotide variants include deletion variants, substitution variants and addition or insertion variants.

As hereinabove indicated, the polynucleotides may have a coding sequence which is a naturally occurring allelic variant of the coding sequences shown in SEQ ID NOS: 17–24. As known in the art, an allelic variant is an alternate form of a polynucleotide sequence which may have a substitution, deletion or addition of one or more nucleotides, which does not substantially alter the function of the encoded enzyme. Also, using directed and other evolution strategies, one may make very minor changes in DNA sequence which can result in major changes in function.

Fragments of the full length gene of the present invention may be used as hybridization probes for a cDNA or a genomic library to isolate the full length DNA and to isolate other DNAs which have a high sequence similarity to the gene or similar biological activity. Probes of this type preferably have at least 10, preferably at least 15, and even more preferably at least 30 bases and may contain, for example, at least 50 or more bases. The probe may also be used to identify a DNA clone corresponding to a full length transcript and a genomic clone or clones that contain the complete gene including regulatory and promotor regions, exons and introns. An example of a screen comprises isolating the coding region of the gene by using the known DNA sequence to synthesize an oligonucleotide probe. Labeled oligonucleotides having a sequence complementary or identical to that of the gene or portion of the gene sequences of the present invention are used to screen a library of genomic DNA to determine which members of the library the probe hybridizes to.

It is also appreciated that such probes can be and are preferably labeled with an analytically detectable reagent to facilitate identification of the probe. Useful reagents include but are not limited to radioactivity, fluorescent dyes or enzymes capable of catalyzing the formation of a detectable product. The probes are thus useful to isolate complementary copies of DNA from other sources or to screen such sources for related sequences.

The present invention further relates to polynucleotides which hybridize to the hereinabove-described sequences if there is at least 70%, preferably at least 90%, and more preferably at least 95% identity between the sequences. The present invention particularly relates to polynucleotides which hybridize under stringent conditions to the hereinabove-described polynucleotides. As herein used, the term "stringent conditions" means hybridization will occur only if there is at least 95% and preferably at least 97% identity between the sequences. The polynucleotides which hybridize to the hereinabove described polynucleotides in a preferred embodiment encode enzymes which either retain substantially the same biological function or activity as the mature enzyme encoded by the DNA of SEQ ID NOS: 17–24.

Alternatively, the polynucleotide may have at least 15 bases, preferably at least 30 bases, and more preferably at least 50 bases which hybridize to any part of a polynucleotide of the present invention and which has an identity thereto, as hereinabove described, and which may or may not retain activity. For example, such polynucleotides may be employed as probes for the polynucleotides of SEQ ID NOS: 17–24, for example, for recovery of the polynucleotide or as a diagnostic probe or as a PCR primer.

Thus, the present invention is directed to polynucleotides having at least a 70% identity, preferably at least 90% identity and more preferably at least a 95% identity to a polynucleotide which encodes the enzymes of SEQ ID NOS:25–32 as well as fragments thereof, which fragments have at least 15 bases, preferably at least 30 bases and most preferably at least 50 bases, which fragments are at least 90% identical, preferably at least 95% identical and most preferably at least 97% identical under stringent conditions to any portion of a polynucleotide of the present invention.

The present invention further relates to enzymes which have the deduced amino acid sequences of SEQ ID NOS: 17–24 as well as fragments, analogs and derivatives of such enzyme.

The terms "fragment," "derivative" and "analog" when referring to the enzymes of SEQ ID NOS:25–32 means enzymes which retain essentially the same biological function or activity as such enzymes. Thus, an analog includes a proprotein which can be activated by cleavage of the proprotein portion to produce an active mature enzyme.

The enzymes of the present invention may be a recombinant enzyme, a natural enzyme or a synthetic enzyme, preferably a recombinant enzyme.

The fragment, derivative or analog of the enzymes of SEQ ID NOS:25–32 may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature enzyme is fused with another compound, such as a compound to increase the half-life of the enzyme (for example, polyethylene glycol), or (iv) one in which the additional amino acids are fused to the mature enzyme, such as a leader or secretory sequence or a sequence which is employed for purification of the mature enzyme or a proprotein sequence. Such fragments, derivatives and analogs are deemed to be within the scope of those skilled in the art from the teachings herein.

The enzymes and polynucleotides of the present invention are preferably provided in an isolated form, and preferably are purified to homogeneity.

The term "isolated" means that the material is removed from its original environment (e.g., the natural environment if it is naturally occurring). For example, a naturally-occurring polynucleotide or enzyme present in a living animal is not isolated, but the same polynucleotide or enzyme, separated from some or all of the coexisting materials in the natural system, is isolated. Such polynucleotides could be part of a vector and/or such polynucleotides or enzymes could be part of a composition, and still be isolated in that such vector or composition is not part of its natural environment.

The enzymes of the present invention include the enzymes of SEQ ID NOS:25–32 (in particular the mature enzyme) as well as enzymes which have at least 70% similarity (preferably at least 70% identity) to the enzymes of SEQ ID NOS:25–32 and more preferably at least 90% similarity (more preferably at least 90% identity) to the enzymes of SEQ ID NOS:25–32 and still more preferably at least 95% similarity (still more preferably at least 95% identity) to the enzymes of SEQ ID NOS:25–32 and also include portions of such enzymes with such portion of the enzyme generally containing at least 30 amino acids and more preferably at least 50 amino acids.

As known in the art "similarity" between two enzymes is determined by comparing the amino acid sequence and its conserved amino acid substitutes of one enzyme to the sequence of a second enzyme.

A variant, i.e. a "fragment", "analog" or "derivative" polypeptide, and reference polypeptide may differ in amino acid sequence by one or more substitutions, additions, deletions, fusions and truncations, which may be present in any combination.

Among preferred variants are those that vary from a reference by conservative amino acid substitutions. Such substitutions are those that substitute a given amino acid in a polypeptide by another amino acid of like characteristics. Typically seen as conservative substitutions are the replacements, one for another, among the aliphatic amino acids Ala, Val, Leu and Ile; interchange of the hydroxyl residues Ser and Thr, exchange of the acidic residues Asp and Glu, substitution between the amide residues Asn and Gln, exchange of the basic residues Lys and Arg and replacements among the aromatic residues Phe, Tyr.

Most highly preferred are variants which retain the same biological function and activity as the reference polypeptide from which it varies.

Fragments or portions of the enzymes of the present invention may be employed for producing the corresponding full-length enzyme by peptide synthesis; therefore, the fragments may be employed as intermediates for producing the full-length enzymes. Fragments or portions of the polynucleotides of the present invention may be used to synthesize full-length polynucleotides of the present invention.

The present invention also relates to vectors which include polynucleotides of the present invention, host cells which are genetically engineered with vectors of the invention and the production of enzymes of the invention by recombinant techniques.

Host cells are genetically engineered (transduced or transformed or transfected) with the vectors of this invention which may be, for example, a cloning vector such as an expression vector. The vector may be, for example, in the form of a plasmid, a phage, etc. The engineered host cells can be cultured in conventional nutrient media modified as appropriate for activating promoters, selecting transformants or amplifying the genes of the present invention. The culture conditions, such as temperature, pH and the like, are those previously used with the host cell selected for expression, and will be apparent to the ordinarily skilled artisan.

The polynucleotides of the present invention may be employed for producing enzymes by recombinant techniques. Thus, for example, the polynucleotide may be included in any one of a variety of expression vectors for expressing an enzyme. Such vectors include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, and pseudorabies. However, any other vector may be used as long as it is replicable and viable in the host.

The appropriate DNA sequence may be inserted into the vector by a variety of procedures. In general, the DNA sequence is inserted into an appropriate restriction endonuclease site(s) by procedures known in the art. Such procedures and others are deemed to be within the scope of those skilled in the art.

The DNA sequence in the expression vector is operatively linked to an appropriate expression control sequence (s) (promoter) to direct MRNA synthesis. As representative examples of such promoters, there may be mentioned: LTR or SV40 promoter, the E. coli. lac or trp, the phage lambda $P_L$ promoter and other promoters known to control expression of genes in prokaryotic or eukaryotic cells or their viruses. The expression vector also contains a ribosome binding site for translation initiation and a transcription terminator. The vector may also include appropriate sequences for amplifying expression.

In addition, the expression vectors preferably contain one or more selectable marker genes to provide a phenotypic trait for selection of transformed host cells such as dihydrofolate reductase or neomycin resistance for eukaryotic cell culture, or such as tetracycline or ampicillin resistance in E. coli.

The vector containing the appropriate DNA sequence as hereinabove described, as well as an appropriate promoter or control sequence, may be employed to transform an appropriate host to permit the host to express the protein.

As representative examples of appropriate hosts, there may be mentioned: bacterial cells, such as E. coli, Streptomyces, Bacillus subtilis; fungal cells, such as yeast; insect cells such as Drosophila S2 and Spodoptera Sf9; animal cells such as CHO, COS or Bowes melanoma; adenoviruses; plant cells, etc. The selection of an appropriate host is deemed to be within the scope of those skilled in the art from the teachings herein.

More particularly, the present invention also includes recombinant constructs comprising one or more of the sequences as broadly described above. The constructs comprise a vector, such as a plasmid or viral vector, into which a sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available. The following vectors are provided by way of example; Bacterial: pQE70, pQE60, pQE-9 (Qiagen), pBluescript II KS, ptrc99a, pKK223-3, pDR540, pRI72T (Pharmacia); Eukaryotic: pXT1, pSG5 (Stratagene) pSVK3, pBPV, pMSG, pSVL SV40 (Pharmacia). However, any other plasmid or vector may be used as long as they are replicable and viable in the host.

Promoter regions can be selected from any desired gene using CAT (chloramphenicol transferase) vectors or other vectors with selectable markers. Two appropriate vectors are pKK232-8 and pCM7. Particular named bacterial promoters include laci, lacZ, T3, T7, gpt, lambda $P_R$, $P_L$ and trp. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art.

In a further embodiment, the present invention relates to host cells containing the above-described constructs. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE-Dextran mediated transfection, or electroporation (Davis, L., Dibner, M., Battey, I., *Basic Methods in Molecular Biology*, (1986)).

The constructs in host cells can be used in a conventional manner to produce the gene product encoded by the recombinant sequence. Alternatively, the enzymes of the invention can be synthetically produced by conventional peptide synthesizers.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook et al., *Molecular Cloning: A Laboratory Manual, Second Edition*, Cold Spring Harbor, N.Y., (1989), the disclosure of which is hereby incorporated by reference.

Transcription of the DNA encoding the enzymes of the present invention by higher eukaryotes is increased by inserting an enhancer sequence into the vector. Enhancers are cis-acting elements of DNA, usually about from 10 to 300 bp that act on a promoter to increase its transcription. Examples include the SV40 enhancer on the late side of the replication origin bp 100 to 270, a cytomegalovirus early promoter enhancer, the polyoma enhancer on the late side of the replication origin, and adenovirus enhancers.

Generally, recombinant expression vectors will include origins of replication and selectable markers permitting transformation of the host cell, e.g., the ampicillin resistance gene of *E. coli* and *S. cerevisiae* TRP1 gene, and a promoter derived from a highly-expressed gene to direct transcription of a downstream structural sequence. Such promoters can be derived from operons encoding glycolytic enzymes such as 3-phosphoglycerate kinase (PGK), α-factor, acid phosphatase, or heat shock proteins, among others. The heterologous structural sequence is assembled in appropriate phase with translation initiation and termination sequences, and preferably, a leader sequence capable of directing secretion of translated enzyme. Optionally, the heterologous sequence can encode a fusion enzyme including an N-terminal identification peptide imparting desired characteristics, e.g., stabilization or simplified purification of expressed recombinant product.

Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transformation include *E. coli, Bacillus subtilis, Salmonella typhimurium* and various species within the genera Pseudomonas, Streptomyces, and Staphylococcus, although others may also be employed as a matter of choice.

As a representative but nonlimiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and pGEM1 (Promega Biotec, Madison, Wis., USA). These pBR322 "backbone" sections are combined with an appropriate promoter and the structural sequence to be expressed.

Following transformation of a suitable host strain and growth of the host strain to an appropriate cell density, the selected promoter is induced by appropriate means (e.g., temperature shift or chemical induction) and cells are cultured for an additional period.

Cells are typically harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents, such methods are well known to those skilled in the art.

Various mammalian cell culture systems can also be employed to express recombinant protein. Examples of mammalian expression systems include the COS-7 lines of monkey kidney fibroblasts, described by Gluzman, *Cell*, 23:175 (1981), and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 splice, and polyadenylation sites may be used to provide the required nontranscribed genetic elements.

The enzyme can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the mature protein. Finally, high performance liquid chromatography (HPLC) can be employed for fmal purification steps.

The enzymes of the present invention may be a naturally purified product, or a product of chemical synthetic procedures, or produced by recombinant techniques from a prokaryotic or eukaryotic host (for example, by bacterial, yeast, higher plant, insect and mammalian cells in culture). Depending upon the host employed in a recombinant production procedure, the enzymes of the present invention may be glycosylated or may be non-glycosylated. Enzymes of the invention may or may not also include an initial methionine amino acid residue.

Transaminases are a group of key enzymes in the metabolism of amino acids and amino sugars and are found in all organisms from microbes to mammals. In the transamination reaction, an amino group is transferred from an amino acid to an α-keto acid. Pyridoxal phosphate is required as a co-factor to mediate the transfer of the amino group without liberation of ammonia.

Amino acids currently have applications as additives to aminal feed, human nutritional supplements, components in infusion solutions, and synthetic intermediates for manufacture of pharmaceuticals and agricultural products. For example, L-glutamic acid is best known as a flavor enhancer for human food. L-lysine and L-methionine are large volume additives to animal feed and human supplements. L-tryptophan and L-threonine have similar potential applications. L-phenylalanine and L-aspartic acid have very important market potential as key components in the manufacture of the low-calorie sweetener aspartame, and other promising low-calorie sweeteners have compositions containing certain amino acids as well. Infusion solutions require a large range of amino acids including those essential ones in human diets.

Transaminases are highly stereoselective, and most use L-amino acids as substrates. Using the approach disclosed in a commonly assigned, copending provisional application Ser. No. 60/008,316, filed on Dec. 7, 1995 and entitled "Combinatorial Enzyme Development," the disclosure of which is incorporated herein by reference in its entirety, one can convert the transaminases of the invention to use D-amino acids as substrates. Such conversion makes possible a broader array of transaminase applications. For instance, D-valine can be used in the manufacture of synthetic pyrethroids. D-phenylglycine and its derivatives can be useful as components of β-lactam antibiotics. Further, the thermostable transaminases have superior stability at higher temperatures and in organic solvents. Thus, they are better suited to utilize either L- and/or D-amino acids for production of optically pure chiral compounds used in pharmaceutical, agricultural, and other chemical manufactures.

There are a number of reasons to employ transaminases in industrial-scale production of amino acids and their derivatives.

1) Transaminases can catalyze stereoselective synthesis of D- or L-amino acids from their corresponding α-keto acids. Therefore no L- or D-isomers are produced, and no resolution is required.

2) Transaminases have uniformly high catalytic rates, capable of converting up to 400 μmoles of substrates per minute per mg enzyme.

3) Many required α-keto acids can be conveniently prepared by chemical synthesis at low cost.

4) The capital investment for an immobilized enzyme process using transaminases is much lower than for a large scale fermentation process, and productivity of the bioreactor is often an order of magnitude higher.

5) The technology is generally applicable to a broad range of D- or L-amino acids because transaminases exist with varying specificities. Such broad scope allows a number of different L- or D-amino acids to be produced with the same equipment and often the same biocatalyst.

Antibodies generated against the enzymes corresponding to a sequence of the present invention can be obtained by direct injection of the enzymes into an animal or by administering the enzymes to an animal, preferably a nonhuman. The antibody so obtained will then bind the enzymes itself. In this manner, even a sequence encoding only a fragment of the enzymes can be used to generate antibodies binding the whole native enzymes. Such antibodies can then be used to isolate the enzyme from cells expressing that enzyme.

For preparation of monoclonal antibodies, any technique which provides antibodies produced by continuous cell line cultures can be used. Examples include the hybridoma technique (Kohler and Milstein, *Nature*, 256:495–497, 1975), the trioma technique, the human B-cell hybridoma technique (Kozbor et al., *Immunology Today* 4:72, 1983), and the EBV-hybridoma technique to produce human monoclonal antibodies (Cole et al., in *Monoclonal Antibodies and Cancer Therapy*, Alan R. Liss, Inc., pp. 77–96, 1985).

Techniques described for the production of single chain antibodies (U.S. Pat. No. 4,946,778) can be adapted to produce single chain antibodies to immunogenic enzyme products of this invention. Also, transgenic mice may be used to express humanized antibodies to immunogenic enzyme products of this invention.

Antibodies generated against an enzyme of the present invention may be used in screening for similar enzymes from other organisms and samples. Such screening techniques are known in the art, for example, one such screening assay is described in Sambrook and Maniatis, *Molecular Cloning: A Laboratory Manual* (2d Ed.), vol. 2:Section 8.49, Cold Spring Harbor Laboratory, 1989, which is hereby incorporated by reference in its entirety.

The present invention will be further described with reference to the following examples; however, it is to be understood that the present invention is not limited to such examples. All parts or amounts, unless otherwise specified, are by weight.

In order to facilitate understanding of the following examples certain frequently occurring methods and/or terms will be described. "Plasmids" are designated by a lower case "p" preceded and/or followed by capital letters and/or numbers. The starting plasmids herein are either commercially available, publicly available on an unrestricted basis, or can be constructed from available plasmids in accord with published procedures. In addition, equivalent plasmids to those described are known in the art and will be apparent to the ordinarily skilled artisan. "Digestion" of DNA refers to catalytic cleavage of the DNA with a restriction enzyme that acts only at certain sequences in the DNA. The various restriction enzymes used herein are commercially available and their reaction conditions, cofactors and other requirements were used as would be known to the ordinarily skilled artisan. For analytical purposes, typically 1 μg of plasmid or DNA fragment is used with about 2 units of enzyme in about 20 μl of buffer solution. For the purpose of isolating DNA fragments for plasmid construction, typically 5 to 50 μg of DNA are digested with 20 to 250 units of enzyme in a larger volume. Appropriate buffers and substrate amounts for particular restriction enzymes are specified by the manufacturer. Incubation times of about 1 hour at 37° C. are ordinarily used, but may vary in accordance with the supplier's instructions. After digestion the reaction is electrophoresed directly on a polyacrylamide gel to isolate the desired fragment.

Size separation of the cleaved fragments is performed using 8 percent polyacrylamide gel described by Goeddel et al., *Nucleic Acids Res.*, 8:4057 (1980).

"Oligonucleotides" refers to either a single stranded polydeoxynucleotide or two complementary polydeoxynucleotide strands which may be chemically synthesized. Such synthetic oligonucleotides have no 5' phosphate and thus will not ligate to another oligonucleotide without adding a phosphate with an ATP in the presence of a kinase. A synthetic oligonucleotide will ligate to a fragment that has not been dephosphorylated.

"Ligation" refers to the process of forming phosphodiester bonds between two double stranded nucleic acid fragments (Maniatis, T., et al., Id., p. 146). Unless otherwise provided, ligation may be accomplished using known buffers and conditions with 10 units of T4 DNA ligase ("ligase")

per 0.5 μg of approximately equimolar amounts of the DNA fragments to be ligated.

Unless otherwise stated, transformation was performed as described in Sambrook and Maniatis, Molecular Cloning: A Laboratory Manual, Cold Spring Harbor Laboratory, 1989.

EXAMPLE 1

Bacterial Expression and Purification of Transaminases and Aminotransferases

DNA encoding the enzymes of the present invention, SEQ ID NOS:25 through 32, were initially amplified from a pBluescript vector containing the DNA by the PCR technique using the primers noted herein. The amplified sequences were then inserted into the respective PQE vector listed beneath the primer sequences, and the enzyme was expressed according to the protocols set forth herein. The genomic DNA has also been used as a template for the PCR amplification, i.e., once a positive clone has been identified and primer sequences determined using the cDNA, it was then possible to return to the genomic DNA and directly amplify the desired sequence(s) there. The 5' and 3' primer sequences and the vector for the respective genes are as follows:

*Aquifex* Aspartate Transaminase A aspa501 5' CCGAGAATTCATTAAAGAGGAGAAAT-TAACTATGATTGAAGACCCTATGGAC (SEQ. ID NO:1)

aspa301 3' CGAAGATCTTTAGCACTTCTCTCAG-GTTC (SEQ. ID NO:2)

vector: pQET1

*Aquifex* Aspartate Aminotransferase B aspb501 5' CCGAGAATTCATTAAAGAGGAGAAAT-TAACTATGGACAGGCTTGAAAAAGTA (SEQ ID NO:3)

aspb301 3' CGGAAGATCTTCAGCTAAGCT-TCTCTAAGAA (SEQ ID NO:4)

vector: pQET1

*Aquifex* Adenosyl-8-amino-7-oxononanoate Aminotransferase ameth501 5' CCGACAATTGATTAAAGAGGAGAAAT-TAACTATGTGGGAATTAGACCCTAAA (SEQ ID NO:5)

ameth301 3' CGGAGGATCCCTACAC-CTCTTTTTCAAGCT (SEQ ID NO:6)

vector: pQET12

*Aquifex* Acetylornithine Aminotransferase aorn 501 5' CCGACAATTGATTAAAGAGGAGAAAT-TAACTATGACATACTTAATGAACAAT (SEQ ID NO:7)

aorn 301 3' CGGAAGATCTTTATGAAGTC-CCTTTCAAG (SEQ ID NO:8)

vector: pQET12

*Ammonifex degensii* Aspartate Aminotransferase adasp 501 5' CCGAGAATTCATTAAAGAGGAGAAAT-TAACTATGCGGAAACTGGCCGAGCGG (SEQ ID NO:9)

adasp 301 3' CGGAGGATCCTTAAAGTGCCGCTTC-GATCAA (SEQ ID NO: 10)

vector: pQET12

*Aquifex* Glucosamine:Fructose-6-phosphate Aminotransferase glut 501 5' CCGACAATTGATTAAAGAGGAGAAAT-TAACTATGTGCGGGATAGTCGGATAC (SEQ ID NO:11)

glut 301 3' CGGAAGATCTTTATTCCACCGTGAC-CGTTTT (SEQ ID NO: 12)

vector: pQET1

*Aquifex* Histadine-phosphate Aminotransferase his 501 5' CCGACAATTGATTAAAGAGGAGAAAT-TAACTATGATACCCCAGAGGATTAAG (SEQ ID NO: 13)

his 301 3' CGGAAGATCTTTAAAGAGAGCT-TGAAAGGGA (SEQ ID NO:14)

vector: pQET1

*Pyrobacullum aerophilum* Branched Chain Aminotransferase bcat 501 5' CCGAGAATTCATTAAAGAGGAGAAAT-TAACIATGAAGCCGTACGCTAAATAT (SEQ ID NO: 15)

bcat 301 3' CGGAAGATCTCTAATACACAGGAGT-GATCCA (SEQ ID NO:16)

vector: PQET1

The restriction enzyme sites indicated correspond to the restriction enzyme sites on the bacterial expression vector indicated for the respective gene (Qiagen, Inc. Chatsworth, Calif.). The pQE vector encodes antibiotic resistance (Amp$^r$), a bacterial origin of replication (ori), an IPTG-regulatable promoter operator (P/O), a ribosome binding site (RBS), a 6His tag and restriction enzyme sites.

The pQE vector was digested with the restriction enzymes indicated. The amplified sequences were ligated into the respective pQE vector and inserted in frame with the sequence encoding for the RBS. The ligation mixture was then used to transform the *E. coli* strain M15/pREP4 (Qiagen, Inc.) by electroporation. M15/pREP4 contains multiple copies of the plasmid pREP4, which expresses the lacI repressor and also confers kanamycin resistance (Kan$^r$). Transformants were identified by their ability to grow on LB plates and ampicillin/kanamycin resistant colonies were selected. Plasmid DNA was isolated and confirmed by restriction analysis. Clones containing the desired constructs were grown overnight (O/N) in liquid culture in LB media supplemented with both Amp (100 ug/ml) and Kan (25 ug/ml). The O/N culture was used to inoculate a large culture at a ratio of 1:100 to 1:250. The cells were grown to an optical density 600 (O.D. $^{600}$) of between 0.4 and 0.6. IPTG ("Isopropyl-B-D-thiogalacto pyranoside") was then added to a fmal concentration of 1 mM. IPTG induces by inactivating the lacI repressor, clearing the P/O leading to increased gene expression. Cells were grown an extra 3 to 4 hours. Cells were then harvested by centrifugation.

The primer sequences set out above may also be employed to isolate the target gene from the deposited material by hybridization techniques described above.

EXAMPLE 2

Isolation of a Selected Clone from the Deposited Genomic Clones

The two oligonucleotide primers corresponding to the gene of interest are used to amplify the gene from the deposited material. A polymerase chain reaction is carried out in 25 μl of reaction mixture with 0.1 μg of the DNA of the gene of interest. The reaction mixture is 1.5–5 mM MgCl$_2$, 0.01% (w/v) gelatin, 20 μM each of DATP, dCTP, dGTP, dTTP, 25 pmol of each primer and 1.25 Unit of Taq polymerase. Thirty cycles of PCR (denaturation at 94° C. for 1 min; annealing at 55° C. for 1 min; elongation at 72° C. for 1 min) are performed with the Perkin-Elmer Cetus 9600 thermal cycler. The amplified product is analyzed by agarose gel electrophoresis and the DNA band with expected molecular weight is excised and purified. The PCR product is verified to be the gene of interest by subcloning and sequencing the DNA product.

Numerous modifications and variations of the present invention are possible in light of the above teachings and, therefore, within the scope of the appended claims, the invention may be practiced otherwise than as particularly described.

What is claimed is:

1. An isolated polynucleotide selected from the group consisting of:
   (a) a polynucleotide encoding an enzyme as set forth in SEQ ID NOS: 25–32;
   (b) a polynucleotide which is complementary to the polynucleotide of (a); and
   (c) a polynucleotide comprising at least 15 consecutive bases of the polynucleotide of (a) or (b) and which hybridize under stringent conditions to a polynucleotide encoding an enzyme as set forth in SEQ ID NOS: 25–32.

2. The polynucleotide of claim 1 wherein the polynucleotide is DNA.

3. The polynucleotide of claim 1 wherein the polynucleotide is RNA.

4. The polynucleotide of claim 2 which encodes an enzyme comprising amino acids 1 to 414 of SEQ ID NO:25.

5. The polynucleotide of claim 2 which encodes an enzyme comprising amino acids 1 to 373 of SEQ ID NO:26.

6. The polynucleotide of claim 2 which encodes an enzyme comprising amino acids 1 to 453 of SEQ ID NO:27.

7. The polynucleotide of claim 2 which encodes an enzyme comprising amino acids 1 to 343 of SEQ ID NO:28.

8. The polynucleotide of claim 2 which encodes an enzyme comprising amino acids 1 to 398 of SEQ ID NO:29.

9. The polynucleotide of claim 2 which encodes an enzyme comprising amino acids 1 to 592 of SEQ ID NO:30.

10. The polynucleotide of claim 2 which encodes an enzyme comprising amino acids 1 to 354 of SEQ ID NO:31.

11. The polynucleotide of claim 2 which encodes an enzyme comprising amino acids 1 to 303 of SEQ ID NO:32.

12. A vector comprising the DNA of claim 2.

13. A host cell comprising the vector of claim 12.

14. A process for producing a polypeptide comprising:
   a) culturing the host cells of claim 13;
   b) expressing from the host cell of claim 13 a polypeptide encoded by said DNA; and
   c) isolating the polypeptide.

15. An enzyme selected from the group consisting of an enzyme comprising the amino acid sequence as set forth in SEQ ID NOS: 25–31 and 32.

16. A method for transferring an amino group from an amino acid to an α-keto acid comprising:
   contacting an amino acid in the presence of an α-keto acid with an enyzme selected from the group consisting of an enzyme having the amino acid sequence set forth in SEQ ID NOS: 25–31 and 32.

* * * * *

UNITED STATES PATENT AND TRADEMARK OFFICE
CERTIFICATE OF CORRECTION

PATENT NO. : 5,814,473
DATED : September 29, 1998
INVENTOR(S) : Warren et al.

Page 1 of 2

Figure 2:
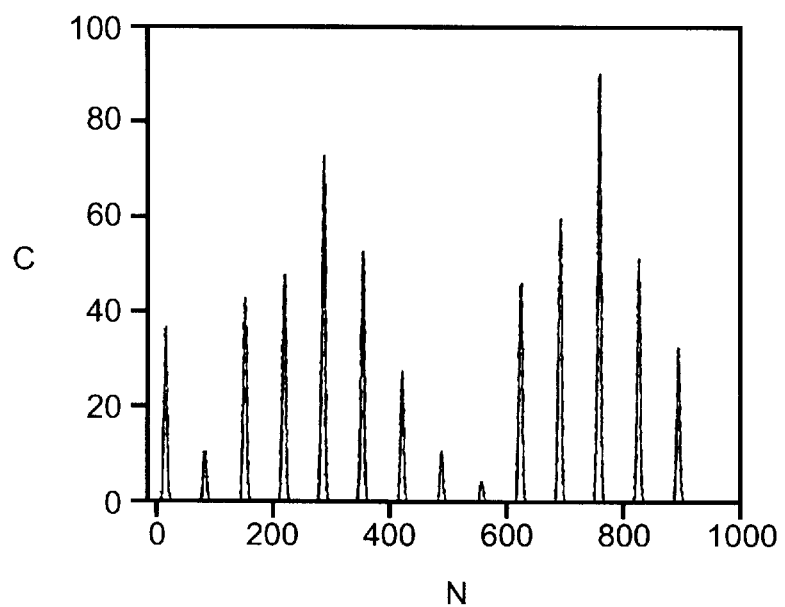

It is certified that error appears in the above-identified patent and that said Letters Patent is hereby corrected as shown below:

In the drawings, replace Fig.1 with Fig.1 shown below, and delete Fig.2.

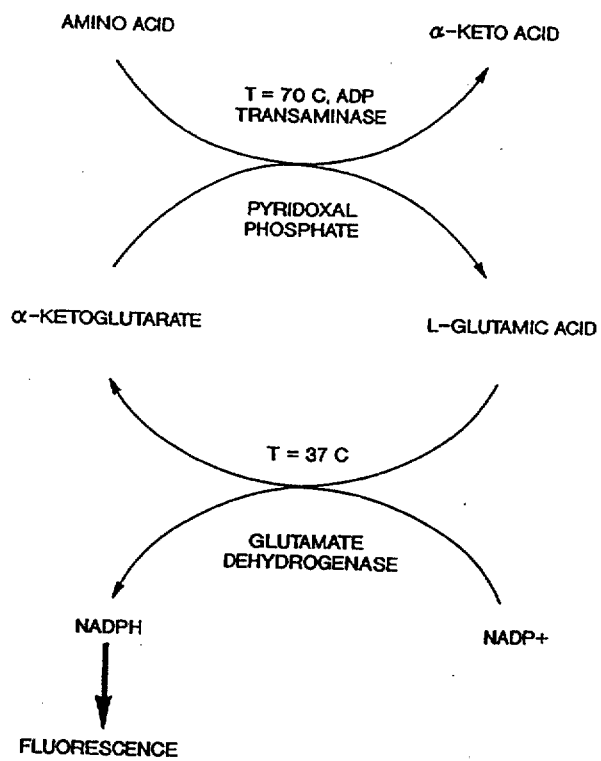

FIG. 1

UNITED STATES PATENT AND TRADEMARK OFFICE
CERTIFICATE OF CORRECTION

PATENT NO. : 5,814,473
DATED : September 29, 1998
INVENTOR(S) : Warren et al.

Page 2 of 2

It is certified that error appears in the above-identified patent and that said Letters Patent is hereby corrected as shown below:

In column 2, line 60, delete "FIGS. 1-8 (" and ")".

Signed and Sealed this

Fifteenth Day of August, 2000

Attest:

Q. TODD DICKINSON

Attesting Officer

Director of Patents and Trademarks

SEQUENCE LISTING ( 1 ) GENERAL INFORMATION:

( i i i ) NUMBER OF SEQUENCES: 32

( 2 ) INFORMATION FOR SEQ ID NO:1:

( i ) SEQUENCE CHARACTERISTICS:
        ( A ) LENGTH: 52 NUCLEOTIDES
        ( B ) TYPE: NUCLEIC ACID
        ( C ) STRANDEDNESS: SINGLE
        ( D ) TOPOLOGY: LINEAR ( i i ) MOLECULE TYPE: cDNA ( x i ) SEQUENCE DESCRIPTION: SEQ ID NO:1:

CCGAGAATTC ATTAAAGAGG AGAAATTAAC TATGATTGAA GACCCTATGG AC    52

( 2 ) INFORMATION FOR SEQ ID NO:2:

( i ) SEQUENCE CHARACTERISTICS:
        ( A ) LENGTH: 31 NUCLEOTIDES
        ( B ) TYPE: NUCLEIC ACID
        ( C ) STRANDEDNESS: SINGLE
        ( D ) TOPOLOGY: LINEAR ( i i ) MOLECULE TYPE: cDNA ( x i ) SEQUENCE DESCRIPTION: SEQ ID NO:2:

CGGAAGATCT TTAAGCACTT CTCTCAGGTT C    31

( 2 ) INFORMATION FOR SEQ ID NO:3:

( i ) SEQUENCE CHARACTERISTICS:
        ( A ) LENGTH: 52 NUCLEOTIDES
        ( B ) TYPE: NUCLEIC ACID
        ( C ) STRANDEDNESS: SINGLE
        ( D ) TOPOLOGY: LINEAR ( i i ) MOLECULE TYPE: cDNA ( x i ) SEQUENCE DESCRIPTION: SEQ ID NO:3:

CCGAGAATTC ATTAAAGAGG AGAAATTAAC TATGGACAGG CTTGAAAAG TA    52

( 2 ) INFORMATION FOR SEQ ID NO:4:

( i ) SEQUENCE CHARACTERISTICS:
        ( A ) LENGTH: 31 NUCLEOTIDES
        ( B ) TYPE: NUCLEIC ACID
        ( C ) STRANDEDNESS: SINGLE
        ( D ) TOPOLOGY: LINEAR ( i i ) MOLECULE TYPE: cDNA ( x i ) SEQUENCE DESCRIPTION: SEQ ID NO:4:

CGGAAGATCT TCAGCTAAGC TTCTCTAAGA A    31

( 2 ) INFORMATION FOR SEQ ID NO:5:

( i ) SEQUENCE CHARACTERISTICS:
        ( A ) LENGTH: 52 NUCLEOTIDES
        ( B ) TYPE: NUCLEIC ACID
        ( C ) STRANDEDNESS: SINGLE
        ( D ) TOPOLOGY: LINEAR (i i) MOLECULE TYPE: cDNA (x i) SEQUENCE DESCRIPTION: SEQ ID NO:5:

CCGACAATTG ATTAAAGAGG AGAAATTAAC TATGTGGGAA TTAGACCCTA AA        52

(2) INFORMATION FOR SEQ ID NO:6:

(i) SEQUENCE CHARACTERISTICS:
        (A) LENGTH: 31 NUCLEOTIDES
        (B) TYPE: NUCLEIC ACID
        (C) STRANDEDNESS: SINGLE
        (D) TOPOLOGY: LINEAR (i i) MOLECULE TYPE: cDNA (x i) SEQUENCE DESCRIPTION: SEQ ID NO:6:

CGGAGGATCC CTACACCTGT TTTTCAAGCT C        31

(2) INFORMATION FOR SEQ ID NO:7:

(i) SEQUENCE CHARACTERISTICS:
        (A) LENGTH: 52 NUCLEOTIDES
        (B) TYPE: NUCLEIC ACID
        (C) STRANDEDNESS: SINGLE
        (D) TOPOLOGY: LINEAR (i i) MOLECULE TYPE: cDNA (x i) SEQUENCE DESCRIPTION: SEQ ID NO:7:

CCGACAATTG ATTAAAGAGG AGAAATTAAC TATGACATAC TTAATGAACA AT        52

(2) INFORMATION FOR SEQ ID NO:8:

(i) SEQUENCE CHARACTERISTICS:
        (A) LENGTH: 31 NUCLEOTIDES
        (B) TYPE: NUCLEIC ACID
        (C) STRANDEDNESS: SINGLE
        (D) TOPOLOGY: LINEAR (i i) MOLECULE TYPE: cDNA (x i) SEQUENCE DESCRIPTION: SEQ ID NO:8:

CGGAAGATCT TTATGAGAAG TCCCTTTCAA G        31

(2) INFORMATION FOR SEQ ID NO:9:

(i) SEQUENCE CHARACTERISTICS:
        (A) LENGTH: 52 NUCLEOTIDES
        (B) TYPE: NUCLEIC ACID
        (C) STRANDEDNESS: SINGLE
        (D) TOPOLOGY: LINEAR (i i) MOLECULE TYPE: cDNA (x i) SEQUENCE DESCRIPTION: SEQ ID NO:9:

CCGAGAATTC ATTAAAGAGG AGAAATTAAC TATGCGGAAA CTGGCCGAGC GG        52

(2) INFORMATION FOR SEQ ID NO:10:

(i) SEQUENCE CHARACTERISTICS:
        (A) LENGTH: 31 NUCLEOTIDES
        (B) TYPE: NUCLEIC ACID
        (C) STRANDEDNESS: SINGLE
        (D) TOPOLOGY: LINEAR (i i) MOLECULE TYPE: cDNA (x i) SEQUENCE DESCRIPTION: SEQ ID NO:10:

CGGAGGATCC TTAAAGTGCC GCTTCGATCA A    31

(2) INFORMATION FOR SEQ ID NO:11:

(i) SEQUENCE CHARACTERISTICS:
        (A) LENGTH: 52 NUCLEOTIDES
        (B) TYPE: NUCLEIC ACID
        (C) STRANDEDNESS: SINGLE
        (D) TOPOLOGY: LINEAR (ii) MOLECULE TYPE: cDNA (xi) SEQUENCE DESCRIPTION: SEQ ID NO:11:

CCGACAATTG ATTAAAGAGG AGAAATTAAC TATGTGCGGG ATAGTCGGAT AC    52

(2) INFORMATION FOR SEQ ID NO:12:

(i) SEQUENCE CHARACTERISTICS:
        (A) LENGTH: 31 NUCLEOTIDES
        (B) TYPE: NUCLEIC ACID
        (C) STRANDEDNESS: SINGLE
        (D) TOPOLOGY: LINEAR (ii) MOLECULE TYPE: cDNA (xi) SEQUENCE DESCRIPTION: SEQ ID NO:12:

CGGAAGATCT TTATTCCACC GTGACCGTTT T    31

(2) INFORMATION FOR SEQ ID NO:13:

(i) SEQUENCE CHARACTERISTICS:
        (A) LENGTH: 52 NUCLEOTIDES
        (B) TYPE: NUCLEIC ACID
        (C) STRANDEDNESS: SINGLE
        (D) TOPOLOGY: LINEAR (ii) MOLECULE TYPE: cDNA (xi) SEQUENCE DESCRIPTION: SEQ ID NO:13:

CCGACAATTG ATTAAAGAGG AGAAATTAAC TATGATACCC CAGAGGATTA AG    52

(2) INFORMATION FOR SEQ ID NO:14:

(i) SEQUENCE CHARACTERISTICS:
        (A) LENGTH: 31 NUCLEOTIDES
        (B) TYPE: NUCLEIC ACID
        (C) STRANDEDNESS: SINGLE
        (D) TOPOLOGY: LINEAR (ii) MOLECULE TYPE: cDNA (xi) SEQUENCE DESCRIPTION: SEQ ID NO:14:

CGGAAGATCT TTAAAGAGAG CTTGAAAGGG A    31

(2) INFORMATION FOR SEQ ID NO:15:

(i) SEQUENCE CHARACTERISTICS:
        (A) LENGTH: 52 NUCLEOTIDES
        (B) TYPE: NUCLEIC ACID
        (C) STRANDEDNESS: SINGLE
        (D) TOPOLOGY: LINEAR (ii) MOLECULE TYPE: cDNA (xi) SEQUENCE DESCRIPTION: SEQ ID NO:15:

CCGAGAATTC ATTAAAGAGG AGAAATTAAC TATGAAGCCG TACGCTAAAT AT    52

(2) INFORMATION FOR SEQ ID NO:16:

( i ) SEQUENCE CHARACTERISTICS:
  ( A ) LENGTH: 31 NUCLEOTIDES
  ( B ) TYPE: NUCLEIC ACID
  ( C ) STRANDEDNESS: SINGLE
  ( D ) TOPOLOGY: LINEAR ( i i ) MOLECULE TYPE: cDNA ( x i ) SEQUENCE DESCRIPTION: SEQ ID NO:16:

CGGAAGATCT CTAATACACA GGAGTGATCC A                                          31

( 2 ) INFORMATION FOR SEQ ID NO:17:

( i ) SEQUENCE CHARACTERISTICS:
    ( A ) LENGTH: 1245 NUCLEOTIDES
    ( B ) TYPE: NUCLEIC ACID
    ( C ) STRANDEDNESS: SINGLE
    ( D ) TOPOLOGY: LINEAR ( i i ) MOLECULE TYPE: GENOMIC DNA ( x i ) SEQUENCE DESCRIPTION: SEQ ID NO:17:

```
ATG ATT GAA GAC CCT ATG GAC TGG GCT TTT CCG AGG ATA AAG AGA CTG      48
Met Ile Glu Asp Pro Met Asp Trp Ala Phe Pro Arg Ile Lys Arg Leu
             5                  10                 15

CCT CAG TAT GTC TTC TCT CTC GTT AAC GAA CTC AAG TAC AAG CTA AGG      96
Pro Gln Tyr Val Phe Ser Leu Val Asn Glu Leu Lys Tyr Lys Leu Arg
         20                  25                 30

CGT GAA GGC GAA GAT GTA GTG GAT CTT GGT ATG GGC AAT CCT AAC ATG     144
Arg Glu Gly Glu Asp Val Val Asp Leu Gly Met Gly Asn Pro Asn Met
         35                  40                 45

CCT CCA GCA AAG CAC ATA ATA GAT AAA CTC TGC GAA GTG GCT CAA AAG     192
Pro Pro Ala Lys His Ile Ile Asp Lys Leu Cys Glu Val Ala Gln Lys
     50                  55                 60

CCG AAC GTT CAC GGA TAT TCT GCG TCA AGG GGC ATA CCA AGA CTG AGA     240
Pro Asn Val His Gly Tyr Ser Ala Ser Arg Gly Ile Pro Arg Leu Arg
 65                  70                 75                 80

AAG GCT ATA TGT AAC TTC TAC GAA GAA AGG TAC GGA GTG AAA CTC GAC     288
Lys Ala Ile Cys Asn Phe Tyr Glu Glu Arg Tyr Gly Val Lys Leu Asp
                 85                  90                 95

CCT GAG AGG GAG GCT ATA CTA ACA ATC GGT GCA AAG GAA GGG TAT TCT     336
Pro Glu Arg Glu Ala Ile Leu Thr Ile Gly Ala Lys Glu Gly Tyr Ser
             100                 105                110

CAT TTG ATG CTT GCG ATG ATA TCT CCG GGT GAT ACG GTA ATA GTT CCT     384
His Leu Met Leu Ala Met Ile Ser Pro Gly Asp Thr Val Ile Val Pro
         115                 120                125

AAT CCC ACC TAT CCT ATT CAC TAT TAC GCT CCC ATA ATT GCA GGA GGG     432
Asn Pro Thr Tyr Pro Ile His Tyr Tyr Ala Pro Ile Ile Ala Gly Gly
     130                 135                 140

GAA GTT CAC TCA ATA CCC CTT AAC TTC TCG GAC GAT CAA GAT CAT CAG     480
Glu Val His Ser Ile Pro Leu Asn Phe Ser Asp Asp Gln Asp His Gln
145                 150                 155                160

GAA GAG TTT TTA AGG AGG CTT TAC GAG ATA GTA AAA ACC GCG ATG CCA     528
Glu Glu Phe Leu Arg Arg Leu Tyr Glu Ile Val Lys Thr Ala Met Pro
                 165                 170                175

AAA CCC AAG GCT GTC GTC ATA AGC TTT CCT CAC AAT CCA ACG ACC ATA     576
Lys Pro Lys Ala Val Val Ile Ser Phe Pro His Asn Pro Thr Thr Ile
             180                 185                190

ACG GTA GAA AAG GAC TTT TTT AAA GAA ATA GTT AAG TTT GCA AAG GAA     624
Thr Val Glu Lys Asp Phe Phe Lys Glu Ile Val Lys Phe Ala Lys Glu
         195                 200                 205

CAC GGT CTC TGG ATA ATA CAC GAT TTT GCG TAT GCG GAT ATA GCC TTT     672
His Gly Leu Trp Ile Ile His Asp Phe Ala Tyr Ala Asp Ile Ala Phe
     210                 215                 220
```

```
GAC  GGT  TAC  AAG  CCC  CCC  TCA  ATA  CTC  GAA  ATA  GAA  GGT  GCT  AAA  GAC       720
Asp  Gly  Tyr  Lys  Pro  Pro  Ser  Ile  Leu  Glu  Ile  Glu  Gly  Ala  Lys  Asp
225            230                      235                      240

GTT  GCG  GTT  GAG  CTC  TAC  TCC  ATG  TCA  AAG  GGC  TTT  TCA  ATG  GCG  GGC       768
Val  Ala  Val  Glu  Leu  Tyr  Ser  Met  Ser  Lys  Gly  Phe  Ser  Met  Ala  Gly
                    245                 250                           255

TGG  AGG  GTA  GCC  TTT  GTC  GTT  GGA  AAC  GAA  ATA  CTC  ATA  AAA  AAC  CTT       816
Trp  Arg  Val  Ala  Phe  Val  Val  Gly  Asn  Glu  Ile  Leu  Ile  Lys  Asn  Leu
               260                      265                      270

GCA  CAC  CTC  AAA  AGC  TAC  TTG  GAT  TAC  GGT  ATA  TTT  ACT  CCC  ATA  CAG       864
Ala  His  Leu  Lys  Ser  Tyr  Leu  Asp  Tyr  Gly  Ile  Phe  Thr  Pro  Ile  Gln
          275                      280                      285

GTG  GCC  TCT  ATT  ATC  GCA  TTA  GAG  AGC  CCC  TAC  GAA  ATC  GTG  GAA  AAA       912
Val  Ala  Ser  Ile  Ile  Ala  Leu  Glu  Ser  Pro  Tyr  Glu  Ile  Val  Glu  Lys
     290                      295                      300

ACC  GCA  AAG  GTT  TAC  CAA  AAA  AGA  AGA  GAC  GTT  CTG  GTG  GAA  GGG  TTA       960
Thr  Ala  Lys  Val  Tyr  Gln  Lys  Arg  Arg  Asp  Val  Leu  Val  Glu  Gly  Leu
305                      310                      315                      320

AAC  AGG  CTC  GGC  TGG  AAA  GTA  AAA  AAA  CCT  AAG  GCT  ACC  ATG  TTC  GTC      1008
Asn  Arg  Leu  Gly  Trp  Lys  Val  Lys  Lys  Pro  Lys  Ala  Thr  Met  Phe  Val
                    325                      330                      335

TGG  GCA  AAG  ATT  CCC  GAA  TGG  ATA  AAT  ATG  AAC  TCT  CTG  GAC  TTT  TCC      1056
Trp  Ala  Lys  Ile  Pro  Glu  Trp  Ile  Asn  Met  Asn  Ser  Leu  Asp  Phe  Ser
               340                      345                      350

TTG  TTC  CTC  CTA  AAA  GAG  GCG  AAG  GTT  GCG  GTA  TCC  CCG  GGT  GTG  GGC      1104
Leu  Phe  Leu  Leu  Lys  Glu  Ala  Lys  Val  Ala  Val  Ser  Pro  Gly  Val  Gly
          355                      360                      365

TTT  GGT  CAG  TAC  GGA  GAG  GGG  TAC  GTA  AGG  TTT  GCA  CTT  GTA  GAA  AAT      1152
Phe  Gly  Gln  Tyr  Gly  Glu  Gly  Tyr  Val  Arg  Phe  Ala  Leu  Val  Glu  Asn
     370                      375                      380

GAA  CAC  AGG  ATC  AGA  CAG  GCT  ATA  AGG  GGA  ATA  AGG  AAA  GCC  TTC  AGA      1200
Glu  His  Arg  Ile  Arg  Gln  Ala  Ile  Arg  Gly  Ile  Arg  Lys  Ala  Phe  Arg
385                      390                      395                      400

AAA  CTC  CAG  AAG  GAG  AGG  AAA  CTT  GAA  CCT  GAG  AGA  AGT  GCT  TAA           1245
Lys  Leu  Gln  Lys  Glu  Arg  Lys  Leu  Glu  Pro  Glu  Arg  Ser  Ala  End
                    405                      410                 414
```

(2) INFORMATION FOR SEQ ID NO:18:

(i) SEQUENCE CHARACTERISTICS:
        (A) LENGTH: 1122 NUCLEOTIDES
        (B) TYPE: NUCLEIC ACID
        (C) STRANDEDNESS: SINGLE
        (D) TOPOLOGY: LINEAR (ii) MOLECULE TYPE: GENOMIC DNA (xi) SEQUENCE DESCRIPTION: SEQ ID NO:18:

```
ATG  GAC  AGG  CTT  GAA  AAA  GTA  TCA  CCC  TTC  ATA  GTA  ATG  GAT  ATC  CTA        48
Met  Asp  Arg  Leu  Glu  Lys  Val  Ser  Pro  Phe  Ile  Val  Met  Asp  Ile  Leu
                    5                        10                       15

GCT  CAG  GCC  CAG  AAG  TAC  GAA  GAC  GTA  GTA  CAC  ATG  GAG  ATA  GGA  GAG        96
Ala  Gln  Ala  Gln  Lys  Tyr  Glu  Asp  Val  Val  His  Met  Glu  Ile  Gly  Glu
               20                       25                       30

CCC  GAT  TTA  GAA  CCG  TCT  CCC  AAG  GTA  ATG  GAA  GCT  CTG  GAA  CGT  GCG       144
Pro  Asp  Leu  Glu  Pro  Ser  Pro  Lys  Val  Met  Glu  Ala  Leu  Glu  Arg  Ala
          35                       40                       45

GTG  AAG  GAA  AAG  ACG  TTC  TTC  TAC  ACC  CCT  GCT  CTG  GGA  CTC  TGG  GAA       192
Val  Lys  Glu  Lys  Thr  Phe  Phe  Tyr  Thr  Pro  Ala  Leu  Gly  Leu  Trp  Glu
     50                       55                       60

CTC  AGG  GAA  AGG  ATA  TCG  GAG  TTT  TAC  AGG  AAA  AAG  TAC  AGC  GTT  GAA       240
Leu  Arg  Glu  Arg  Ile  Ser  Glu  Phe  Tyr  Arg  Lys  Lys  Tyr  Ser  Val  Glu
```

```
        65                            70                            75                            80
GTT   TCT   CCA   GAG   AGA   GTC   ATC   GTA   ACT   ACC   GGA   ACT   TCG   GGA   GCG   TTT      288
Val   Ser   Pro   Glu   Arg   Val   Ile   Val   Thr   Thr   Gly   Thr   Ser   Gly   Ala   Phe
                         85                            90                            95

CTC   GTA   GCC   TAC   GCC   GTA   ACA   CTA   AAT   GCG   GGA   GAG   AAG   ATA   ATC   CTC      336
Leu   Val   Ala   Tyr   Ala   Val   Thr   Leu   Asn   Ala   Gly   Glu   Lys   Ile   Ile   Leu
                  100                           105                           110

CCA   GAC   CCC   TCT   TAC   CCC   TGT   TAC   AAA   AAC   TTT   GCC   TAC   CTC   TTA   GAC      384
Pro   Asp   Pro   Ser   Tyr   Pro   Cys   Tyr   Lys   Asn   Phe   Ala   Tyr   Leu   Leu   Asp
            115                           120                           125

GCT   CAG   CCG   GTT   TTC   GTA   AAC   GTT   GAC   AAG   GAA   ACG   AAT   TAC   GAA   GTA      432
Ala   Gln   Pro   Val   Phe   Val   Asn   Val   Asp   Lys   Glu   Thr   Asn   Tyr   Glu   Val
      130                           135                           140

AGG   AAA   GAG   ATG   ATA   GAA   GAC   ATT   GAT   GCG   AAA   GCC   CTT   CAC   ATT   TCC      480
Arg   Lys   Glu   Met   Ile   Glu   Asp   Ile   Asp   Ala   Lys   Ala   Leu   His   Ile   Ser
145                           150                           155                           160

TCG   CCT   CAA   AAC   CCT   ACG   GGC   ACA   CTC   TAC   TCA   CCT   GAA   ACC   CTG   AAG      528
Ser   Pro   Gln   Asn   Pro   Thr   Gly   Thr   Leu   Tyr   Ser   Pro   Glu   Thr   Leu   Lys
                        165                           170                           175

GAA   CTT   GCG   GAG   TAC   TGC   GAA   GAG   AAG   GGT   ATG   TAC   TTC   ATA   TCC   GAC      576
Glu   Leu   Ala   Glu   Tyr   Cys   Glu   Glu   Lys   Gly   Met   Tyr   Phe   Ile   Ser   Asp
                  180                           185                           190

GAG   ATT   TAC   CAC   GGA   CTC   GTT   TAC   GAA   GGT   AGG   GAG   CAC   ACA   GCA   CTT      624
Glu   Ile   Tyr   His   Gly   Leu   Val   Tyr   Glu   Gly   Arg   Glu   His   Thr   Ala   Leu
            195                           200                           205

GAG   TTC   TCT   GAC   AGG   GCT   ATT   GTC   ATA   AAC   GGG   TTT   TCT   AAG   TAC   TTC      672
Glu   Phe   Ser   Asp   Arg   Ala   Ile   Val   Ile   Asn   Gly   Phe   Ser   Lys   Tyr   Phe
      210                           215                           220

TGT   ATG   CCA   GGT   TTC   AGG   ATA   GGG   TGG   ATG   ATA   GTT   CCG   GAA   GAA   CTC      720
Cys   Met   Pro   Gly   Phe   Arg   Ile   Gly   Trp   Met   Ile   Val   Pro   Glu   Glu   Leu
225                           230                           235                           240

GTG   AGA   AAG   GCG   GAA   ATA   GTA   ATT   CAG   AAC   GTA   TTT   ATA   TCT   GCC   CCG      768
Val   Arg   Lys   Ala   Glu   Ile   Val   Ile   Gln   Asn   Val   Phe   Ile   Ser   Ala   Pro
                        245                           250                           255

ACG   CTC   AGT   CAG   TAC   GCC   GCC   CTT   GAG   GCT   TTT   GAT   TAC   GAG   TAT   TTG      816
Thr   Leu   Ser   Gln   Tyr   Ala   Ala   Leu   Glu   Ala   Phe   Asp   Tyr   Glu   Tyr   Leu
                  260                           265                           270

GAG   AAG   GTA   AGA   AAA   ACC   TTT   GAA   GAG   AGG   AGG   AAC   TTC   CTT   TAT   GGG      864
Glu   Lys   Val   Arg   Lys   Thr   Phe   Glu   Glu   Arg   Arg   Asn   Phe   Leu   Tyr   Gly
            275                           280                           285

GAA   CTG   AAA   AAA   CTC   TTC   AAG   ATA   GAC   GCG   AAA   CCT   CAG   GGA   GCT   TTT      912
Glu   Leu   Lys   Lys   Leu   Phe   Lys   Ile   Asp   Ala   Lys   Pro   Gln   Gly   Ala   Phe
      290                           295                           300

TAC   GTA   TGG   GCA   AAC   ATA   AGT   GAT   TAC   TCC   ACA   GAT   AGC   TAC   GAA   TTT      960
Tyr   Val   Trp   Ala   Asn   Ile   Ser   Asp   Tyr   Ser   Thr   Asp   Ser   Tyr   Glu   Phe
305                           310                           315                           320

GCT   TTA   AAA   CTT   TTA   AGG   GAG   GCG   AGG   GTG   GCG   GTA   ACG   CCC   GGG   GTG     1008
Ala   Leu   Lys   Leu   Leu   Arg   Glu   Ala   Arg   Val   Ala   Val   Thr   Pro   Gly   Val
                        325                           330                           335

GAC   TTT   GGA   AAA   AAC   AAA   ACG   AAG   GAG   TAT   ATA   AGG   TTT   GCT   TAT   ACG     1056
Asp   Phe   Gly   Lys   Asn   Lys   Thr   Lys   Glu   Tyr   Ile   Arg   Phe   Ala   Tyr   Thr
                  340                           345                           350

AGA   AAG   ATA   GAA   GAA   CTT   AAG   GAG   GGC   GTT   GAA   AGG   ATA   AAG   AAG   TTC     1104
Arg   Lys   Ile   Glu   Glu   Leu   Lys   Glu   Gly   Val   Glu   Arg   Ile   Lys   Lys   Phe
            355                           360                           365

TTA   GAG   AAG   CTT   AGC   TGA                                                                 1122
Leu   Glu   Lys   Leu   Ser   End
370
```

( 2 ) INFORMATION FOR SEQ ID NO:19:

(i) SEQUENCE CHARACTERISTICS:
  (A) LENGTH: 1362 NUCLEOTIDES
  (B) TYPE: NUCLEIC ACID
  (C) STRANDEDNESS: SINGLE
  (D) TOPOLOGY: LINEAR (ii) MOLECULE TYPE: GENOMIC DNA (xi) SEQUENCE DESCRIPTION: SEQ ID NO:19:

| | | | | | | | | | | | | | | | | |
|---|---|---|---|---|---|---|---|---|---|---|---|---|---|---|---|---|
| ATG | TGG | GAA | TTA | GAC | CCT | AAA | ACG | CTC | GAA | AAG | TGG | GAC | AAG | GAG | TAC | 48 |
| Met | Trp | Glu | Leu | Asp | Pro | Lys | Thr | Leu | Glu | Lys | Trp | Asp | Lys | Glu | Tyr | |
| | | | | 5 | | | | | 10 | | | | | 15 | | |
| TTC | TGG | CAT | CCA | TTT | ACC | CAG | ATG | AAA | GTC | TAC | AGA | GAA | GAA | GAA | AAC | 96 |
| Phe | Trp | His | Pro | Phe | Thr | Gln | Met | Lys | Val | Tyr | Arg | Glu | Glu | Glu | Asn | |
| | | | 20 | | | | | 25 | | | | | 30 | | | |
| CTG | ATA | TTT | GAA | CGC | GGA | GAA | GGC | GTT | TAC | CTG | TGG | GAC | ATA | TAC | GGC | 144 |
| Leu | Ile | Phe | Glu | Arg | Gly | Glu | Gly | Val | Tyr | Leu | Trp | Asp | Ile | Tyr | Gly | |
| | | 35 | | | | | 40 | | | | | 45 | | | | |
| AGG | AAG | TAT | ATA | GAT | GCC | ATA | TCT | TCC | CTC | TGG | TGC | AAC | GTC | CAC | GGA | 192 |
| Arg | Lys | Tyr | Ile | Asp | Ala | Ile | Ser | Ser | Leu | Trp | Cys | Asn | Val | His | Gly | |
| | 50 | | | | | 55 | | | | | 60 | | | | | |
| CAT | AAC | CAC | CCT | AAA | CTG | AAC | AAC | GCA | GTT | ATG | AAA | CAG | CTC | TGT | AAG | 240 |
| His | Asn | His | Pro | Lys | Leu | Asn | Asn | Ala | Val | Met | Lys | Gln | Leu | Cys | Lys | |
| 65 | | | | | 70 | | | | | 75 | | | | | 80 | |
| GTA | GCT | CAC | ACA | ACT | ACT | CTG | GGA | AGT | TCC | AAC | GTT | CCC | GCC | ATA | CTC | 288 |
| Val | Ala | His | Thr | Thr | Thr | Leu | Gly | Ser | Ser | Asn | Val | Pro | Ala | Ile | Leu | |
| | | | | 85 | | | | | 90 | | | | | 95 | | |
| CTT | GCA | AAG | AAG | CTT | GTA | GAA | ATT | TCT | CCT | GAA | GGA | TTA | AAC | AAG | GTC | 336 |
| Leu | Ala | Lys | Lys | Leu | Val | Glu | Ile | Ser | Pro | Glu | Gly | Leu | Asn | Lys | Val | |
| | | | 100 | | | | | 105 | | | | | 110 | | | |
| TTT | TAC | TCC | GAA | GAC | GGT | GCG | GAA | GCA | GTA | GAG | ATA | GCG | ATA | AAG | ATG | 384 |
| Phe | Tyr | Ser | Glu | Asp | Gly | Ala | Glu | Ala | Val | Glu | Ile | Ala | Ile | Lys | Met | |
| | | 115 | | | | | 120 | | | | | 125 | | | | |
| GCT | TAT | CAC | TAC | TGG | AAG | AAC | AAG | GGA | GTT | AAA | GGG | AAA | AAC | GTT | TTC | 432 |
| Ala | Tyr | His | Tyr | Trp | Lys | Asn | Lys | Gly | Val | Lys | Gly | Lys | Asn | Val | Phe | |
| | 130 | | | | | 135 | | | | | 140 | | | | | |
| ATA | ACG | CTT | TCC | GAA | GCC | TAC | CAC | GGG | GAT | ACT | GTA | GGA | GCG | GTT | AGC | 480 |
| Ile | Thr | Leu | Ser | Glu | Ala | Tyr | His | Gly | Asp | Thr | Val | Gly | Ala | Val | Ser | |
| 145 | | | | | 150 | | | | | 155 | | | | | 160 | |
| GTA | GGG | GGT | ATA | GAA | CTC | TTC | CAC | GGA | ACT | TAT | AAA | GAT | CTC | CTT | TTC | 528 |
| Val | Gly | Gly | Ile | Glu | Leu | Phe | His | Gly | Thr | Tyr | Lys | Asp | Leu | Leu | Phe | |
| | | | | 165 | | | | | 170 | | | | | 175 | | |
| AAG | ACT | ATA | AAA | CTC | CCA | TCT | CCT | TAC | CTG | TAC | TGC | AAG | GAA | AAG | TAC | 576 |
| Lys | Thr | Ile | Lys | Leu | Pro | Ser | Pro | Tyr | Leu | Tyr | Cys | Lys | Glu | Lys | Tyr | |
| | | | 180 | | | | | 185 | | | | | 190 | | | |
| GGG | GAA | CTC | TGC | CCT | GAG | TGC | ACG | GCA | GAT | TTA | TTA | AAA | CAA | CTG | GAA | 624 |
| Gly | Glu | Leu | Cys | Pro | Glu | Cys | Thr | Ala | Asp | Leu | Leu | Lys | Gln | Leu | Glu | |
| | | 195 | | | | | 200 | | | | | 205 | | | | |
| GAT | ATC | CTG | AAG | TCG | CGG | GAA | GAT | ATC | GTT | GCG | GTC | ATT | ATG | GAA | GCG | 672 |
| Asp | Ile | Leu | Lys | Ser | Arg | Glu | Asp | Ile | Val | Ala | Val | Ile | Met | Glu | Ala | |
| | | 210 | | | | | 215 | | | | | 220 | | | | |
| GGA | ATT | CAG | GCA | GCC | GCG | GGA | ATG | CTC | CCC | TTC | CCT | CCG | GGA | TTT | TTG | 720 |
| Gly | Ile | Gln | Ala | Ala | Ala | Gly | Met | Leu | Pro | Phe | Pro | Pro | Gly | Phe | Leu | |
| 225 | | | | | 230 | | | | | 235 | | | | | 240 | |
| AAA | GGC | GTA | AGG | GAG | CTT | ACG | AAG | AAA | TAC | GAC | ACT | TTA | ATG | ATA | GTT | 768 |
| Lys | Gly | Val | Arg | Glu | Leu | Thr | Lys | Lys | Tyr | Asp | Thr | Leu | Met | Ile | Val | |
| | | | | 245 | | | | | 250 | | | | | 255 | | |
| GAC | GAG | GTT | GCC | ACG | GGA | TTT | GGC | AGG | ACG | GGA | ACG | ATG | TTT | TAC | TGT | 816 |
| Asp | Glu | Val | Ala | Thr | Gly | Phe | Gly | Arg | Thr | Gly | Thr | Met | Phe | Tyr | Cys | |
| | | | | 260 | | | | | 265 | | | | | 270 | | |
| GAG | CAG | GAA | GGA | GTC | AGT | CCG | GAC | TTT | ATG | TGT | CTA | GGT | AAG | GGT | ATA | 864 |

```
Glu Gln Glu Gly Val Ser Pro Asp Phe Met Cys Leu Gly Lys Gly Ile
    275                 280                 285

ACC GGA GGG TAC CTC CCG CTT GCT GCG ACA CTC ACA ACG GAC GAG GTG        912
Thr Gly Gly Tyr Leu Pro Leu Ala Ala Thr Leu Thr Thr Asp Glu Val
    290                 295                 300

TTC AAT GCC TTT TTA GGT GAG TTC GGG GAG GCA AAG CAC TTT TAC CAC        960
Phe Asn Ala Phe Leu Gly Glu Phe Gly Glu Ala Lys His Phe Tyr His
305                 310                 315                 320

GGG CAC ACC TAC ACT GGA AAT AAC CTC GCC TGT TCC GTT GCA CTC GCA       1008
Gly His Thr Tyr Thr Gly Asn Asn Leu Ala Cys Ser Val Ala Leu Ala
                325                 330                 335

AAC TTA GAA GTT TTT GAG GAA GAA AGA ACT TTA GAG AAG CTC CAA CCA       1056
Asn Leu Glu Val Phe Glu Glu Glu Arg Thr Leu Glu Lys Leu Gln Pro
            340                 345                 350

AAG ATA AAG CTT TTA AAG GAA AGG CTT CAG GAG TTC TGG GAA CTC AAG       1104
Lys Ile Lys Leu Leu Lys Glu Arg Leu Gln Glu Phe Trp Glu Leu Lys
        355                 360                 365

CAC GTT GGA GAT GTT AGA CAG CTA GGT TTT ATG GCT GGA ATA GAG CTG       1152
His Val Gly Asp Val Arg Gln Leu Gly Phe Met Ala Gly Ile Glu Leu
    370                 375                 380

GTG AAG GAC AAA GAA AAG GGA GAA CCT TTC CCT TAC GGT GAA AGG ACG       1200
Val Lys Asp Lys Glu Lys Gly Glu Pro Phe Pro Tyr Gly Glu Arg Thr
385                 390                 395                 400

GGA TTT AAG GTG GCT TAC AAG TGC AGG GAA AAA GGG GTG TTT TTG AGA       1248
Gly Phe Lys Val Ala Tyr Lys Cys Arg Glu Lys Gly Val Phe Leu Arg
                405                 410                 415

CCG CTC GGA GAC GTT ATG GTA TTG ATG ATG CCT CTT GTA ATA GAG GAA       1296
Pro Leu Gly Asp Val Met Val Leu Met Met Pro Leu Val Ile Glu Glu
            420                 425                 430

GAC GAA ATG AAC TAC GTT ATT GAT ACA CTT AAA TGG GCA ATT AAA GAG       1344
Asp Glu Met Asn Tyr Val Ile Asp Thr Leu Lys Trp Ala Ile Lys Glu
        435                 440                 445

CTT GAA AAA GAG GTG TAG                                                1362
Leu Glu Lys Glu Val End
    450
```

( 2 ) INFORMATION FOR SEQ ID NO:20:

( i ) SEQUENCE CHARACTERISTICS:
        ( A ) LENGTH: 1032 NUCLEOTIDES
        ( B ) TYPE: NUCLEIC ACID
        ( C ) STRANDEDNESS: SINGLE
        ( D ) TOPOLOGY: LINEAR ( i i ) MOLECULE TYPE: GENOMIC DNA ( x i ) SEQUENCE DESCRIPTION: SEQ ID NO:20:

```
ATG ACA TAC TTA ATG AAC AAT TAC GCA AGG TTG CCC GTA AAG TTT GTA         48
Met Thr Tyr Leu Met Asn Asn Tyr Ala Arg Leu Pro Val Lys Phe Val
                5                  10                  15

AGG GGA AAA GGT GTT TAC CTG TAC GAT GAG GAA GGA AAG GAG TAT CTT         96
Arg Gly Lys Gly Val Tyr Leu Tyr Asp Glu Glu Gly Lys Glu Tyr Leu
            20                  25                  30

GAC TTT GTC TCC GGT ATA GGC GTC AAC TCC CTC GGT CAC GCT TAC CCA        144
Asp Phe Val Ser Gly Ile Gly Val Asn Ser Leu Gly His Ala Tyr Pro
        35                  40                  45

AAA CTC ACA GAA GCT CTA AAA GAA CAG GTT GAG AAA CTC CTC CAC GTT        192
Lys Leu Thr Glu Ala Leu Lys Glu Gln Val Glu Lys Leu Leu His Val
    50                  55                  60

TCA AAT CTT TAC GAA AAC CCG TGG CAG GAA GAA CTG GCT CAC AAA CTT        240
Ser Asn Leu Tyr Glu Asn Pro Trp Gln Glu Glu Leu Ala His Lys Leu
65                  70                  75                  80
```

| | | | | | | | | | | | | | | | | |
|---|---|---|---|---|---|---|---|---|---|---|---|---|---|---|---|---|
| GTA | AAA | CAC | TTC | TGG | ACA | GAA | GGG | AAG | GTA | TTT | TTC | GCA | AAC | AGC | GGA | 288 |
| Val | Lys | His | Phe | Trp | Thr | Glu | Gly | Lys | Val | Phe | Phe | Ala | Asn | Ser | Gly | |
| | | | | 85 | | | | 90 | | | | | | | 95 | |
| ACG | GAA | AGT | GTA | GAG | GCG | GCT | ATA | AAG | CTC | GCA | AGG | AAG | TAC | TGG | AGG | 336 |
| Thr | Glu | Ser | Val | Glu | Ala | Ala | Ile | Lys | Leu | Ala | Arg | Lys | Tyr | Trp | Arg | |
| | | | 100 | | | | 105 | | | | | 110 | | | | |
| GAT | AAA | GGA | AAG | AAC | AAG | TGG | AAG | TTT | ATA | TCC | TTT | GAA | AAC | TCT | TTC | 384 |
| Asp | Lys | Gly | Lys | Asn | Lys | Trp | Lys | Phe | Ile | Ser | Phe | Glu | Asn | Ser | Phe | |
| | | 115 | | | | | 120 | | | | | 125 | | | | |
| CAC | GGG | AGA | ACC | TAC | GGT | AGC | CTC | TCC | GCA | ACG | GGA | CAG | CCA | AAG | TTC | 432 |
| His | Gly | Arg | Thr | Tyr | Gly | Ser | Leu | Ser | Ala | Thr | Gly | Gln | Pro | Lys | Phe | |
| | 130 | | | | | 135 | | | | | 140 | | | | | |
| CAC | AAA | GGC | TTT | GAA | CCT | CTA | GTT | CCT | GGA | TTT | TCT | TAC | GCA | AAG | CTG | 480 |
| His | Lys | Gly | Phe | Glu | Pro | Leu | Val | Pro | Gly | Phe | Ser | Tyr | Ala | Lys | Leu | |
| 145 | | | | | 150 | | | | | 155 | | | | | 160 | |
| AAC | GAT | ATA | GAC | AGC | GTT | TAC | AAA | CTC | CTA | GAC | GAG | GAA | ACC | GCG | GGG | 528 |
| Asn | Asp | Ile | Asp | Ser | Val | Tyr | Lys | Leu | Leu | Asp | Glu | Glu | Thr | Ala | Gly | |
| | | | | 165 | | | | | 170 | | | | | 175 | | |
| ATA | ATT | ATT | GAA | GTT | ATA | CAA | GGA | GAG | GGC | GGA | GTA | AAC | GAG | GCG | AGT | 576 |
| Ile | Ile | Ile | Glu | Val | Ile | Gln | Gly | Glu | Gly | Gly | Val | Asn | Glu | Ala | Ser | |
| | | | 180 | | | | | 185 | | | | | 190 | | | |
| GAG | GAT | TTT | CTA | AGT | AAA | CTC | CAG | GAA | ATT | TGT | AAA | GAA | AAA | GAT | GTG | 624 |
| Glu | Asp | Phe | Leu | Ser | Lys | Leu | Gln | Glu | Ile | Cys | Lys | Glu | Lys | Asp | Val | |
| | | 195 | | | | | 200 | | | | | 205 | | | | |
| CTC | TTA | ATT | ATA | GAC | GAA | GTG | CAA | ACG | GGA | ATA | GGA | AGG | ACC | GGG | GAA | 672 |
| Leu | Leu | Ile | Ile | Asp | Glu | Val | Gln | Thr | Gly | Ile | Gly | Arg | Thr | Gly | Glu | |
| | 210 | | | | | 215 | | | | | 220 | | | | | |
| TTC | TAC | GCA | TAT | CAA | CAC | TTC | AAT | CTA | AAA | CCG | GAC | GTA | ATT | GCG | CTT | 720 |
| Phe | Tyr | Ala | Tyr | Gln | His | Phe | Asn | Leu | Lys | Pro | Asp | Val | Ile | Ala | Leu | |
| 225 | | | | | 230 | | | | | 235 | | | | | 240 | |
| GCG | AAG | GGA | CTC | GGA | GGA | GGT | GTG | CCA | ATA | GGT | GCC | ATC | CTT | GCA | AGG | 768 |
| Ala | Lys | Gly | Leu | Gly | Gly | Gly | Val | Pro | Ile | Gly | Ala | Ile | Leu | Ala | Arg | |
| | | | | 245 | | | | | 250 | | | | | 255 | | |
| GAA | GAA | GTG | GCC | CAG | AGC | TTT | ACT | CCC | GGC | TCC | CAC | GGC | TCT | ACC | TTC | 816 |
| Glu | Glu | Val | Ala | Gln | Ser | Phe | Thr | Pro | Gly | Ser | His | Gly | Ser | Thr | Phe | |
| | | | 260 | | | | | 265 | | | | | 270 | | | |
| GGA | GGA | AAC | CCC | TTA | GCC | TGC | AGG | GCG | GGA | ACA | GTG | GTA | GTA | GAT | GAA | 864 |
| Gly | Gly | Asn | Pro | Leu | Ala | Cys | Arg | Ala | Gly | Thr | Val | Val | Val | Asp | Glu | |
| | | 275 | | | | | 280 | | | | | 285 | | | | |
| GTT | GAA | AAA | CTC | CTG | CCT | CAC | GTA | AGG | GAA | GTG | GGG | AAT | TAC | TTC | AAA | 912 |
| Val | Glu | Lys | Leu | Leu | Pro | His | Val | Arg | Glu | Val | Gly | Asn | Tyr | Phe | Lys | |
| | 290 | | | | | 295 | | | | | 300 | | | | | |
| GAA | AAA | CTG | AAG | GAA | CTC | GGC | AAA | GGA | AAG | GTA | AAG | GGA | AGA | GGA | TTG | 960 |
| Glu | Lys | Leu | Lys | Glu | Leu | Gly | Lys | Gly | Lys | Val | Lys | Gly | Arg | Gly | Leu | |
| 305 | | | | | 310 | | | | | 315 | | | | | 320 | |
| ATG | CTC | GGT | CTT | GAA | CTT | GAA | AGA | GAG | TGT | AAA | GAT | TAC | GTT | CTC | AAG | 1008 |
| Met | Leu | Gly | Leu | Glu | Leu | Glu | Arg | Glu | Cys | Lys | Asp | Tyr | Val | Leu | Lys | |
| | | | | 325 | | | | | 330 | | | | | 335 | | |
| GCT | CTT | GAA | AGG | GAC | TTC | TCA | TAA | | | | | | | | | 1032 |
| Ala | Leu | Glu | Arg | Asp | Phe | Ser | End | | | | | | | | | |
| | | | 340 | | | | | | | | | | | | | |

( 2 ) INFORMATION FOR SEQ ID NO:21:

( i ) SEQUENCE CHARACTERISTICS:
        ( A ) LENGTH: 1197 NUCLEOTIDES
        ( B ) TYPE: NUCLEIC ACID
        ( C ) STRANDEDNESS: SINGLE
        ( D ) TOPOLOGY: LINEAR ( i i ) MOLECULE TYPE: GENOMIC DNA ( x i ) SEQUENCE DESCRIPTION: SEQ ID NO:21:

```
ATG CGG AAA CTG GCC GAG CGG GCG CAG AAA CTG AGC CCC TCT CCC ACC
Met Arg Lys Leu Ala Glu Arg Ala Gln Lys Leu Ser Pro Ser Pro Thr
                    5                   10                  15

CTC TCG GTG GAC ACC AAG GCC AAG GAG CTT TTG CGG CAG GGG GAA AGG
Leu Ser Val Asp Thr Lys Ala Lys Glu Leu Leu Arg Gln Gly Glu Arg
                20                  25                  30

GTC ATC AAT TTC GGG GCG GGG GAG CCG GAC TTC GAT ACA CCG GAA CAC
Val Ile Asn Phe Gly Ala Gly Glu Pro Asp Phe Asp Thr Pro Glu His
            35                  40                  45

ATC AAG GAA GCG GCG AAG CGA GCT TTA GAT CAG GGC TTC ACC AAG TAC
Ile Lys Glu Ala Ala Lys Arg Ala Leu Asp Gln Gly Phe Thr Lys Tyr
        50                  55                  60

ACG CCG GTG GCT GGG ATC TTA CCT CTT CGG GAG GCC ATA TGC GAG AAG
Thr Pro Val Ala Gly Ile Leu Pro Leu Arg Glu Ala Ile Cys Glu Lys
65                  70                  75                  80

CTT TAC CGC GAC AAT CAA CTG GAA TAC AGC CCG AAT GAG ATC GTG GTC
Leu Tyr Arg Asp Asn Gln Leu Glu Tyr Ser Pro Asn Glu Ile Val Val
                85                  90                  95

TCC TGT GGC GCC AAG CAT TCT ATT TTC AAC GCT CTG CAG GTC CTC CTG
Ser Cys Gly Ala Lys His Ser Ile Phe Asn Ala Leu Gln Val Leu Leu
            100                 105                 110

GAC CCG GGG GAC GAG GTG ATA ATC CCC GTC CCC TAC TGG ACT TCC TAT
Asp Pro Gly Asp Glu Val Ile Ile Pro Val Pro Tyr Trp Thr Ser Tyr
        115                 120                 125

CCG GAG CAG GTG AAG CTG GCG GGA GGG GTG CCG GTT TTC GTC CCC ACC
Pro Glu Gln Val Lys Leu Ala Gly Gly Val Pro Val Phe Val Pro Thr
130                 135                 140

TCT CCC GAG AAC GAC TTC AAG CTC AGG CCG GAA GAT CTA CGT GCG GCT
Ser Pro Glu Asn Asp Phe Lys Leu Arg Pro Glu Asp Leu Arg Ala Ala
145                 150                 155                 160

GTA ACC CCG CGC ACC CGC CTT TTG ATC CTC AAT TCC CCG GCC AAC CCC
Val Thr Pro Arg Thr Arg Leu Leu Ile Leu Asn Ser Pro Ala Asn Pro
                165                 170                 175

ACA GGC ACC GTT TAC CGC CGG GAG GAA CTT ATC GGC TTA GCG GAG GTA
Thr Gly Thr Val Tyr Arg Arg Glu Glu Leu Ile Gly Leu Ala Glu Val
            180                 185                 190

GCC CTG GAG GCC GAC CTA TGG ATC TTG TCG GAC GAG ATC TAC GAA AAG
Ala Leu Glu Ala Asp Leu Trp Ile Leu Ser Asp Glu Ile Tyr Glu Lys
        195                 200                 205

CTG ATC TAC GAC GGG ATG GAG CAC GTG AGC ATA GCC GCG CTC GAC CCG
Leu Ile Tyr Asp Gly Met Glu His Val Ser Ile Ala Ala Leu Asp Pro
210                 215                 220

GAG GTC AAA AAG CGC ACG ATT GTG GTA AAC GGT GTT TCC AAG GCT TAC
Glu Val Lys Lys Arg Thr Ile Val Val Asn Gly Val Ser Lys Ala Tyr
225                 230                 235                 240

GCC ATG ACC GGT TGG CGC ATA GGT TAT GCT GCC GCT CCC CGG CCG ATA
Ala Met Thr Gly Trp Arg Ile Gly Tyr Ala Ala Ala Pro Arg Pro Ile
                245                 250                 255

GCC CAG GCC ATG ACC AAC CTC CAA AGC CAC AGT ACC TCT AAC CCC ACT
Ala Gln Ala Met Thr Asn Leu Gln Ser His Ser Thr Ser Asn Pro Thr
            260                 265                 270

TCC GTA GCC CAG GCG GCG GCG CTG GCC GCT CTG AAG GGG CCA CAA GAG
Ser Val Ala Gln Ala Ala Ala Leu Ala Ala Leu Lys Gly Pro Gln Glu
        275                 280                 285

CCG GTG GAG AAC ATG CGC CGG GCT TTT CAA AAG CGG CGG GAT TTC ATC
Pro Val Glu Asn Met Arg Arg Ala Phe Gln Lys Arg Arg Asp Phe Ile
290                 295                 300

TGG CAG TAC CTA AAC TCC TTA CCC GGA GTG CGC TGC CCC AAA CCT TTA
Trp Gln Tyr Leu Asn Ser Leu Pro Gly Val Arg Cys Pro Lys Pro Leu
305                 310                 315                 320
```

```
GGG  GCC  TTT  TAC  GTC  TTT  CCA  GAA  GTT  GAG  CGG  GCT  TTT  GGG  CCG  CCG                1
Gly  Ala  Phe  Tyr  Val  Phe  Pro  Glu  Val  Glu  Arg  Ala  Phe  Gly  Pro  Pro
               325                          330                      335

TCT  AAA  AGG  ACG  GGA  AAT  ACT  ACC  GCT  AGC  GAC  CTG  GCC  CTT  TTC  CTC                1
Ser  Lys  Arg  Thr  Gly  Asn  Thr  Thr  Ala  Ser  Asp  Leu  Ala  Leu  Phe  Leu
               340                          345                      350

CTG  GAA  GAG  ATA  AAA  GTG  GCC  ACC  GTG  GCT  GGG  GCT  GCC  TTT  GGG  GAC                1
Leu  Glu  Glu  Ile  Lys  Val  Ala  Thr  Val  Ala  Gly  Ala  Ala  Phe  Gly  Asp
               355                          360                      365

GAT  CGC  TAC  CTG  CGC  TTT  TCC  TAC  GCC  CTG  CGG  CTG  GAA  GAT  ATC  GAA                1
Asp  Arg  Tyr  Leu  Arg  Phe  Ser  Tyr  Ala  Leu  Arg  Leu  Glu  Asp  Ile  Glu
          370                     375                          380

GAG  GGG  ATG  CAA  CGG  TTT  AAA  GAA  TTG  ATC  GAA  GCG  GCA  CTT  TAA                     1
Glu  Gly  Met  Gln  Arg  Phe  Lys  Glu  Leu  Ile  Glu  Ala  Ala  Leu  End
385                     390                     395
```

( 2 ) INFORMATION FOR SEQ ID NO:22:

( i ) SEQUENCE CHARACTERISTICS:
     ( A ) LENGTH: 1779 NUCLEOTIDES
     ( B ) TYPE: NUCLEIC ACID
     ( C ) STRANDEDNESS: SINGLE
     ( D ) TOPOLOGY: LINEAR ( i i ) MOLECULE TYPE: GENOMIC DNA ( x i ) SEQUENCE DESCRIPTION: SEQ ID NO:22:

```
ATG  TGC  GGG  ATA  GTC  GGA  TAC  GTA  GGG  AGG  GAT  TTA  GCC  CTT  CCT  ATA
Met  Cys  Gly  Ile  Val  Gly  Tyr  Val  Gly  Arg  Asp  Leu  Ala  Leu  Pro  Ile
                    5                        10                       15

GTC  CTC  GGA  GCT  CTT  GAG  AGA  CTC  GAA  TAC  AGG  GGT  TAC  GAC  TCC  GCG
Val  Leu  Gly  Ala  Leu  Glu  Arg  Leu  Glu  Tyr  Arg  Gly  Tyr  Asp  Ser  Ala
               20                          25                       30

GGA  GTT  GCC  CTT  ATA  GAA  GAC  GGG  AAA  CTC  ATA  GTT  GAA  AAG  AAG  AAG
Gly  Val  Ala  Leu  Ile  Glu  Asp  Gly  Lys  Leu  Ile  Val  Glu  Lys  Lys  Lys
               35                          40                       45

GGA  AAG  ATA  AGG  GAA  CTC  GTT  AAA  GCG  CTA  TGG  GGA  AAG  GAT  TAC  AAG
Gly  Lys  Ile  Arg  Glu  Leu  Val  Lys  Ala  Leu  Trp  Gly  Lys  Asp  Tyr  Lys
     50                          55                       60

GCT  AAA  ACG  GGT  ATA  GGT  CAC  ACA  CGC  TGG  GCA  ACC  CAC  GGA  AAG  CCC
Ala  Lys  Thr  Gly  Ile  Gly  His  Thr  Arg  Trp  Ala  Thr  His  Gly  Lys  Pro
65                     70                          75                       80

ACG  GAC  GAG  AAC  GCC  CAC  CCC  CAC  ACC  GAC  GAA  AAA  GGT  GAG  TTT  GCA
Thr  Asp  Glu  Asn  Ala  His  Pro  His  Thr  Asp  Glu  Lys  Gly  Glu  Phe  Ala
                    85                          90                       95

GTA  GTT  CAC  AAC  GGG  ATA  ATA  GAA  AAC  TAC  TTA  GAA  CTA  AAA  GAG  GAA
Val  Val  His  Asn  Gly  Ile  Ile  Glu  Asn  Tyr  Leu  Glu  Leu  Lys  Glu  Glu
               100                         105                      110

CTA  AAG  AAG  GAA  GGT  GTA  AAG  TTC  AGG  TCC  GAA  ACA  GAC  ACA  GAA  GTT
Leu  Lys  Lys  Glu  Gly  Val  Lys  Phe  Arg  Ser  Glu  Thr  Asp  Thr  Glu  Val
          115                         120                      125

ATA  GCC  CAC  CTC  ATA  GCG  AAG  AAC  TAC  AGG  GGG  GAC  TTA  CTG  GAG  GCC
Ile  Ala  His  Leu  Ile  Ala  Lys  Asn  Tyr  Arg  Gly  Asp  Leu  Leu  Glu  Ala
          130                         135                      140

GTT  TTA  AAA  ACC  GTA  AAG  AAA  TTA  AAG  GGT  GCT  TTT  GCC  TTT  GCG  GTT
Val  Leu  Lys  Thr  Val  Lys  Lys  Leu  Lys  Gly  Ala  Phe  Ala  Phe  Ala  Val
145                     150                         155                      160

ATA  ACG  GTT  CAC  GAA  CCA  AAC  AGA  CTA  ATA  GGA  GTG  AAG  CAG  GGG  AGT
Ile  Thr  Val  His  Glu  Pro  Asn  Arg  Leu  Ile  Gly  Val  Lys  Gln  Gly  Ser
                    165                         170                      175

CCT  TTA  ATC  GTC  GGA  CTC  GGA  GAA  GGA  GAA  AAC  TTC  CTC  GCT  TCA  GAT
Pro  Leu  Ile  Val  Gly  Leu  Gly  Glu  Gly  Glu  Asn  Phe  Leu  Ala  Ser  Asp
```

```
                            180                         185                           190
ATT  CCC  GCA  ATA  CTT  CCT  TAC  ACG  AAA  AAG  ATT  ATT  GTT  CTT  GAT  GAC
Ile  Pro  Ala  Ile  Leu  Pro  Tyr  Thr  Lys  Lys  Ile  Ile  Val  Leu  Asp  Asp
          195                      200                      205

GGG  GAA  ATA  GCG  GAC  CTG  ACT  CCC  GAC  ACT  GTG  AAC  ATT  TAC  AAC  TTT
Gly  Glu  Ile  Ala  Asp  Leu  Thr  Pro  Asp  Thr  Val  Asn  Ile  Tyr  Asn  Phe
     210                      215                      220

GAG  GGA  GAG  CCC  GTT  TCA  AAG  GAA  GTA  ATG  ATT  ACG  CCC  TGG  GAT  CTT
Glu  Gly  Glu  Pro  Val  Ser  Lys  Glu  Val  Met  Ile  Thr  Pro  Trp  Asp  Leu
225                      230                      235                      240

GTT  TCT  GCG  GAA  AAG  GGT  GGT  TTT  AAA  CAC  TTC  ATG  CTA  AAA  GAG  ATA
Val  Ser  Ala  Glu  Lys  Gly  Gly  Phe  Lys  His  Phe  Met  Leu  Lys  Glu  Ile
               245                      250                      255

TAC  GAA  CAG  CCC  AAA  GCC  ATA  AAC  GAC  ACA  CTC  AAG  GGT  TTC  CTC  TCA
Tyr  Glu  Gln  Pro  Lys  Ala  Ile  Asn  Asp  Thr  Leu  Lys  Gly  Phe  Leu  Ser
               260                      265                      270

ACC  GAA  GAC  GCA  ATA  CCC  TTT  AAG  TTA  AAA  GAC  TTC  AGA  AGG  GTT  TTA
Thr  Glu  Asp  Ala  Ile  Pro  Phe  Lys  Leu  Lys  Asp  Phe  Arg  Arg  Val  Leu
          275                      280                      285

ATA  ATA  GCG  TGC  GGG  ACC  TCT  TAC  CAC  GCG  GGC  TTC  GTC  GGA  AAG  TAC
Ile  Ile  Ala  Cys  Gly  Thr  Ser  Tyr  His  Ala  Gly  Phe  Val  Gly  Lys  Tyr
     290                      295                      300

TGG  ATA  GAG  AGA  TTT  GCA  GGT  GTT  CCC  ACA  GAG  GTA  ATT  TAC  GCT  TCG
Trp  Ile  Glu  Arg  Phe  Ala  Gly  Val  Pro  Thr  Glu  Val  Ile  Tyr  Ala  Ser
305                      310                      315                      320

GAA  TTC  AGG  TAT  GCG  GAC  GTT  CCC  GTT  TCG  GAC  AAG  GAT  ATC  GTT  ATC    1
Glu  Phe  Arg  Tyr  Ala  Asp  Val  Pro  Val  Ser  Asp  Lys  Asp  Ile  Val  Ile
               325                      330                      335

GGA  ATT  TCC  CAG  TCA  GGA  GAG  ACC  GCT  GAC  ACA  AAG  TTT  GCC  CTT  CAG    1
Gly  Ile  Ser  Gln  Ser  Gly  Glu  Thr  Ala  Asp  Thr  Lys  Phe  Ala  Leu  Gln
               340                      345                      350

TCC  GCA  AAG  GAA  AAG  GGA  GCC  TTT  ACC  GTG  GGA  CTC  GTA  AAC  GTA  GTG    1
Ser  Ala  Lys  Glu  Lys  Gly  Ala  Phe  Thr  Val  Gly  Leu  Val  Asn  Val  Val
               355                      360                      365

GGA  AGT  GCC  ATA  GAC  AGG  GAG  TCG  GAC  TTT  TCC  CTT  CAC  ACA  CAT  GCG    1
Gly  Ser  Ala  Ile  Asp  Arg  Glu  Ser  Asp  Phe  Ser  Leu  His  Thr  His  Ala
     370                      375                      380

GGA  CCC  GAA  ATA  GGC  GTG  GCG  GCT  ACA  AAG  ACC  TTC  ACC  GCA  CAG  TTC    1
Gly  Pro  Glu  Ile  Gly  Val  Ala  Ala  Thr  Lys  Thr  Phe  Thr  Ala  Gln  Phe
385                      390                      395                      400

ACC  GCA  CTC  TAC  GCC  CTT  TCG  GTA  AGG  GAA  AGT  GAG  GAG  AGG  GAA  AAT    1
Thr  Ala  Leu  Tyr  Ala  Leu  Ser  Val  Arg  Glu  Ser  Glu  Glu  Arg  Glu  Asn
               405                      410                      415

CTA  ATA  AGA  CTC  CTT  GAA  AAG  GTT  CCA  TCA  CTC  GTT  GAA  CAA  ACA  CTG    1
Leu  Ile  Arg  Leu  Leu  Glu  Lys  Val  Pro  Ser  Leu  Val  Glu  Gln  Thr  Leu
               420                      425                      430

AAC  ACC  GCA  GAA  GAA  GTG  GAG  AAG  GTA  GCG  GAA  AAG  TAC  ATG  AAA  AAG    1
Asn  Thr  Ala  Glu  Glu  Val  Glu  Lys  Val  Ala  Glu  Lys  Tyr  Met  Lys  Lys
          435                      440                      445

AAA  AAC  ATG  CTT  TAC  CTC  GGA  AGG  TAC  TTA  AAT  TAC  CCC  ATA  GCG  CTG    1
Lys  Asn  Met  Leu  Tyr  Leu  Gly  Arg  Tyr  Leu  Asn  Tyr  Pro  Ile  Ala  Leu
          450                      455                      460

GAG  GGA  GCT  CTT  AAA  CTT  AAA  GAA  ATT  TCT  TAC  ATA  CAC  GCG  GAA  GGT    1
Glu  Gly  Ala  Leu  Lys  Leu  Lys  Glu  Ile  Ser  Tyr  Ile  His  Ala  Glu  Gly
465                      470                      475                      480

TAT  CCC  GCA  GGG  GAG  ATG  AAG  CAC  GGT  CCC  ATA  GCC  CTC  ATA  GAC  GAA    1
Tyr  Pro  Ala  Gly  Glu  Met  Lys  His  Gly  Pro  Ile  Ala  Leu  Ile  Asp  Glu
                    485                      490                      495

AAC  ATG  CCG  GTT  GTG  GTA  ATC  GCA  CCG  AAA  GAC  AGG  GTT  TAC  GAG  AAG    1
Asn  Met  Pro  Val  Val  Val  Ile  Ala  Pro  Lys  Asp  Arg  Val  Tyr  Glu  Lys
```

```
                    5 0 0                          5 0 5                          5 1 0
ATA   CTC   TCA   AAC   GTA   GAA   GAG   GTT   CTC   GCA   AGA   AAG   GGA   AGG   GTT   ATT            1
Ile   Leu   Ser   Asn   Val   Glu   Glu   Val   Leu   Ala   Arg   Lys   Gly   Arg   Val   Ile
            5 1 5                         5 2 0                         5 2 5

TCT   GTA   GGC   TTT   AAA   GGA   GAC   GAA   ACT   CTC   AAA   AGC   AAA   TCC   GAG   AGC            1
Ser   Val   Gly   Phe   Lys   Gly   Asp   Glu   Thr   Leu   Lys   Ser   Lys   Ser   Glu   Ser
            5 3 0                         5 3 5                         5 4 0

GTT   ATG   GAA   ATC   CCG   AAG   GCA   GAA   GAA   CCG   ATA   ACT   CCT   TTC   TTG   ACG            1
Val   Met   Glu   Ile   Pro   Lys   Ala   Glu   Glu   Pro   Ile   Thr   Pro   Phe   Leu   Thr
5 4 5                         5 5 0                         5 5 5                         5 6 0

GTA   ATA   CCC   CTG   CAA   CTC   TTT   GCC   TAC   TTT   ATA   GCG   AGC   AAA   CTG   GGA            1
Val   Ile   Pro   Leu   Gln   Leu   Phe   Ala   Tyr   Phe   Ile   Ala   Ser   Lys   Leu   Gly
                        5 6 5                         5 7 0                         5 7 5

CTG   GAT   GTG   GAT   CAG   CCG   AGA   AAT   CTC   GCC   AAA   ACG   GTC   ACG   GTG   GAA            1
Leu   Asp   Val   Asp   Gln   Pro   Arg   Asn   Leu   Ala   Lys   Thr   Val   Thr   Val   Glu
                        5 8 0                         5 8 5                         5 9 0

TAA                                                                                                      1
End
```

( 2 ) INFORMATION FOR SEQ ID NO:23:

( i ) SEQUENCE CHARACTERISTICS:
        ( A ) LENGTH: 1065 NUCLEOTIDES
        ( B ) TYPE: NUCLEIC ACID
        ( C ) STRANDEDNESS: SINGLE
        ( D ) TOPOLOGY: LINEAR ( i i ) MOLECULE TYPE: GENOMIC DNA ( x i ) SEQUENCE DESCRIPTION: SEQ ID NO:23:

```
ATG   ATA   CCC   CAG   AGG   ATT   AAG   GAA   CTT   GAA   GCT   TAC   AAG   ACG   GAG   GTC
Met   Ile   Pro   Gln   Arg   Ile   Lys   Glu   Leu   Glu   Ala   Tyr   Lys   Thr   Glu   Val
                        5                           1 0                          1 5

ACT   CCC   GCC   TCC   GTC   AGG   CTT   TCC   TCT   AAC   GAA   TTC   CCC   TAC   GAC   TTT
Thr   Pro   Ala   Ser   Val   Arg   Leu   Ser   Ser   Asn   Glu   Phe   Pro   Tyr   Asp   Phe
                        2 0                          2 5                          3 0

CCC   GAG   GAG   ATA   AAA   CAA   AGG   GCC   TTA   GAA   GAA   TTA   AAA   AAG   GTT   CCC
Pro   Glu   Glu   Ile   Lys   Gln   Arg   Ala   Leu   Glu   Glu   Leu   Lys   Lys   Val   Pro
            3 5                          4 0                          4 5

TTG   AAC   AAA   TAC   CCA   GAC   CCC   GAA   GCG   AAA   GAG   TTA   AAA   GCG   GTT   CTT
Leu   Asn   Lys   Tyr   Pro   Asp   Pro   Glu   Ala   Lys   Glu   Leu   Lys   Ala   Val   Leu
            5 0                          5 5                          6 0

GCG   GAT   TTT   TTC   GGC   GTT   AAG   GAA   GAA   AAT   TTA   GTT   CTC   GGT   AAC   GGT
Ala   Asp   Phe   Phe   Gly   Val   Lys   Glu   Glu   Asn   Leu   Val   Leu   Gly   Asn   Gly
6 5                           7 0                          7 5                          8 0

TCG   GAC   GAA   CTC   ATA   TAC   TAC   CTC   TCA   ATA   GCT   ATA   GGT   GAA   CTT   TAC
Ser   Asp   Glu   Leu   Ile   Tyr   Tyr   Leu   Ser   Ile   Ala   Ile   Gly   Glu   Leu   Tyr
                        8 5                          9 0                          9 5

ATA   CCC   GTT   TAC   ATA   CCT   GTT   CCC   ACC   TTT   CCC   ATG   TAC   GAG   ATA   AGT
Ile   Pro   Val   Tyr   Ile   Pro   Val   Pro   Thr   Phe   Pro   Met   Tyr   Glu   Ile   Ser
                        1 0 0                        1 0 5                        1 1 0

GCG   AAA   GTT   CTC   GGA   AGA   CCC   CTC   GTA   AAG   GTT   CAA   CTG   GAC   GAA   AAC
Ala   Lys   Val   Leu   Gly   Arg   Pro   Leu   Val   Lys   Val   Gln   Leu   Asp   Glu   Asn
            1 1 5                        1 2 0                        1 2 5

TTT   GAT   ATA   GAC   TTA   GAA   AGA   AGT   ATT   GAA   TTA   ATA   GAG   AAA   GAA   AAA
Phe   Asp   Ile   Asp   Leu   Glu   Arg   Ser   Ile   Glu   Leu   Ile   Glu   Lys   Glu   Lys
            1 3 0                        1 3 5                        1 4 0

CCC   GTT   CTC   GGG   TAC   TTT   GCT   TAC   CCA   AAC   AAC   CCC   ACG   GGA   AAC   CTC
Pro   Val   Leu   Gly   Tyr   Phe   Ala   Tyr   Pro   Asn   Asn   Pro   Thr   Gly   Asn   Leu
1 4 5                         1 5 0                        1 5 5                        1 6 0

TTT   TCC   AGG   GGA   AAG   ATT   GAG   GAG   ATA   AGA   AAC   AGG   GGT   GTT   TTC   TGT
Phe   Ser   Arg   Gly   Lys   Ile   Glu   Glu   Ile   Arg   Asn   Arg   Gly   Val   Phe   Cys
```

```
                          165                              170                              175
GTA  ATA  GAC  GAA  GCC  TAC  TAT  CAT  TAC  TCC  GGA  GAA  ACC  TTT  CTG  GAA
Val  Ile  Asp  Glu  Ala  Tyr  Tyr  His  Tyr  Ser  Gly  Glu  Thr  Phe  Leu  Glu
               180                         185                         190

GAC  GCG  CTC  AAA  AGG  GAA  GAT  ACG  GTA  GTT  TTG  AGG  ACA  CTT  TCA  AAA
Asp  Ala  Leu  Lys  Arg  Glu  Asp  Thr  Val  Val  Leu  Arg  Thr  Leu  Ser  Lys
               195                         200                         205

ATC  GGT  ATG  GCG  AGT  TTA  AGG  GTA  GGG  ATT  TTA  ATA  GGG  AAG  GGG  GAA
Ile  Gly  Met  Ala  Ser  Leu  Arg  Val  Gly  Ile  Leu  Ile  Gly  Lys  Gly  Glu
      210                         215                         220

ATC  GTC  TCA  GAA  ATT  AAC  AAG  GTG  AGA  CTC  CCC  TTC  AAC  GTG  ACC  TAC
Ile  Val  Ser  Glu  Ile  Asn  Lys  Val  Arg  Leu  Pro  Phe  Asn  Val  Thr  Tyr
225                         230                         235                         240

CCC  TCT  CAG  GTG  ATG  GCA  AAA  GTT  CTC  CTC  ACG  GAG  GGA  AGA  GAA  TTC
Pro  Ser  Gln  Val  Met  Ala  Lys  Val  Leu  Leu  Thr  Glu  Gly  Arg  Glu  Phe
               245                         250                         255

CTA  ATG  GAA  AAG  ATA  CAG  GAG  GTT  GTA  ACA  GAG  CGA  GAA  AGG  ATG  TAC
Leu  Met  Glu  Lys  Ile  Gln  Glu  Val  Val  Thr  Glu  Arg  Glu  Arg  Met  Tyr
               260                         265                         270

GAC  GAA  ATG  AAG  AAA  ATA  GAA  GGA  GTT  GAG  GTT  TTT  CCG  AGT  AAG  GCT
Asp  Glu  Met  Lys  Lys  Ile  Glu  Gly  Val  Glu  Val  Phe  Pro  Ser  Lys  Ala
               275                         280                         285

AAC  TTC  TTG  CTT  TTC  AGA  ACG  CCT  TAC  CCC  GCC  CAC  GAG  GTT  TAT  CAG
Asn  Phe  Leu  Leu  Phe  Arg  Thr  Pro  Tyr  Pro  Ala  His  Glu  Val  Tyr  Gln
               290                         295                         300

GAG  CTA  CTG  AAA  AGG  GAT  GTC  CTC  GTC  AGG  AAC  GTA  TCT  TAC  ATG  GAA
Glu  Leu  Leu  Lys  Arg  Asp  Val  Leu  Val  Arg  Asn  Val  Ser  Tyr  Met  Glu
305                         310                         315                         320

GGA  CTC  CAA  AAG  TGC  CTC  AGG  GTA  AGC  GTA  GGG  AAA  CCG  GAA  GAA  AAC      1
Gly  Leu  Gln  Lys  Cys  Leu  Arg  Val  Ser  Val  Gly  Lys  Pro  Glu  Glu  Asn
               325                         330                         335

AAC  AAG  TTT  CTG  GAA  GCA  CTG  GAG  GAG  AGT  ATA  AAA  TCC  CTT  TCA  AGC      1
Asn  Lys  Phe  Leu  Glu  Ala  Leu  Glu  Glu  Ser  Ile  Lys  Ser  Leu  Ser  Ser
               340                         345                         350

TCT  CTT  TAA                                                                        1
Ser  Leu  End
```

( 2 ) INFORMATION FOR SEQ ID NO:24:

( i ) SEQUENCE CHARACTERISTICS:
        ( A ) LENGTH: 912 NUCLEOTIDES
        ( B ) TYPE: NUCLEIC ACID
        ( C ) STRANDEDNESS: SINGLE
        ( D ) TOPOLOGY: LINEAR ( i i ) MOLECULE TYPE: GENOMIC DNA ( x i ) SEQUENCE DESCRIPTION: SEQ ID NO:24:

```
ATG  AAG  CCG  TAC  GCT  AAA  TAT  ATC  TGG  CTT  GAC  GGC  AGA  ATA  CTT  AAG
Met  Lys  Pro  Tyr  Ala  Lys  Tyr  Ile  Trp  Leu  Asp  Gly  Arg  Ile  Leu  Lys
                    5                         10                         15

TGG  GAA  GAC  GCG  AAA  ATA  CAC  GTG  TTG  ACT  CAC  GCG  CTT  CAC  TAC  GGA
Trp  Glu  Asp  Ala  Lys  Ile  His  Val  Leu  Thr  His  Ala  Leu  His  Tyr  Gly
               20                         25                         30

ACC  TCT  ATA  TTC  GAG  GGA  ATA  AGA  GGG  TAT  TGG  AAC  GGC  GAT  AAT  TTG
Thr  Ser  Ile  Phe  Glu  Gly  Ile  Arg  Gly  Tyr  Trp  Asn  Gly  Asp  Asn  Leu
               35                         40                         45

CTC  GTC  TTT  AGG  TTA  GAA  GAA  CAC  ATC  GAC  CGC  ATG  TAC  AGA  TCG  GCT
Leu  Val  Phe  Arg  Leu  Glu  Glu  His  Ile  Asp  Arg  Met  Tyr  Arg  Ser  Ala
          50                         55                         60

AAG  ATA  CTA  GGC  ATA  AAT  ATT  CCG  TAT  ACA  AGA  GAG  GAA  GTC  CGC  CAA
Lys  Ile  Leu  Gly  Ile  Asn  Ile  Pro  Tyr  Thr  Arg  Glu  Glu  Val  Arg  Gln
```

| | 65 | | | | 70 | | | | | 75 | | | | | 80 |
|---|---|---|---|---|---|---|---|---|---|---|---|---|---|---|---|
| GCT | GTA | CTA | GAG | ACC | ATA | AAG | GCT | AAT | AAC | TTC | CGA | GAG | GAT | GTC | TAC |
| Ala | Val | Leu | Glu | Thr | Ile | Lys | Ala | Asn | Asn | Phe | Arg | Glu | Asp | Val | Tyr |
| | | | | 85 | | | | | 90 | | | | | 95 | |
| ATA | AGA | CCT | GTG | GCG | TTT | GTC | GCC | TCG | CAG | ACG | GTG | ACG | CTT | GAC | ATA |
| Ile | Arg | Pro | Val | Ala | Phe | Val | Ala | Ser | Gln | Thr | Val | Thr | Leu | Asp | Ile |
| | | | 100 | | | | | 105 | | | | | 110 | | |
| AGA | AAT | TTG | GAA | GTC | TCC | CTC | GCG | GTT | ATT | GTA | TTC | CCA | TTT | GGC | AAA |
| Arg | Asn | Leu | Glu | Val | Ser | Leu | Ala | Val | Ile | Val | Phe | Pro | Phe | Gly | Lys |
| | | 115 | | | | | 120 | | | | | 125 | | | |
| TAC | CTC | TCG | CCC | AAC | GGC | ATT | AAG | GCA | ACG | ATT | GTA | AGC | TGG | CGT | AGA |
| Tyr | Leu | Ser | Pro | Asn | Gly | Ile | Lys | Ala | Thr | Ile | Val | Ser | Trp | Arg | Arg |
| | 130 | | | | | 135 | | | | | 140 | | | | |
| GTA | CAT | AAT | ACA | ATG | CTC | CCT | GTG | ATG | GCA | AAA | ATC | GGC | GGT | ATA | TAT |
| Val | His | Asn | Thr | Met | Leu | Pro | Val | Met | Ala | Lys | Ile | Gly | Gly | Ile | Tyr |
| 145 | | | | | 150 | | | | | 155 | | | | | 160 |
| GTA | AAC | TCT | GTA | CTT | GCG | CTT | GTA | GAG | GCT | AGA | AGC | AGG | GGA | TTT | GAC |
| Val | Asn | Ser | Val | Leu | Ala | Leu | Val | Glu | Ala | Arg | Ser | Arg | Gly | Phe | Asp |
| | | | | 165 | | | | | 170 | | | | | 175 | |
| GAG | GCT | TTA | TTA | ATG | GAC | GTT | AAC | GGT | TAT | GTT | GTT | GAG | GGT | TCT | GGA |
| Glu | Ala | Leu | Leu | Met | Asp | Val | Asn | Gly | Tyr | Val | Val | Glu | Gly | Ser | Gly |
| | | | 180 | | | | | 185 | | | | | 190 | | |
| GAG | AAT | ATT | TTC | ATT | GTC | AGA | GGT | GGA | AGG | CTT | TTC | ACG | CCG | CCA | GTA |
| Glu | Asn | Ile | Phe | Ile | Val | Arg | Gly | Gly | Arg | Leu | Phe | Thr | Pro | Pro | Val |
| | | 195 | | | | | 200 | | | | | 205 | | | |
| CAC | GAA | TCT | ATC | CTC | GAG | GGA | ATT | ACG | AGG | GAT | ACG | GTA | ATA | AAG | CTC |
| His | Glu | Ser | Ile | Leu | Glu | Gly | Ile | Thr | Arg | Asp | Thr | Val | Ile | Lys | Leu |
| | 210 | | | | | 215 | | | | | 220 | | | | |
| AGC | GGG | GAT | GTG | GGA | CTT | CGG | GTG | GAG | GAA | AAG | CCT | ATT | ACG | AGG | GAG |
| Ser | Gly | Asp | Val | Gly | Leu | Arg | Val | Glu | Glu | Lys | Pro | Ile | Thr | Arg | Glu |
| 225 | | | | | 230 | | | | | 235 | | | | | 240 |
| GAG | GTG | TAT | ACA | GCC | GAC | GAG | GTG | TTT | TTA | GTA | GGA | ACC | GCC | GCA | GAG |
| Glu | Val | Tyr | Thr | Ala | Asp | Glu | Val | Phe | Leu | Val | Gly | Thr | Ala | Ala | Glu |
| | | | | 245 | | | | | 250 | | | | | 255 | |
| ATA | ACG | CCA | GTG | GTG | GAG | GTT | GAC | GGC | AGA | ACA | ATC | GGC | ACA | GGC | AAG |
| Ile | Thr | Pro | Val | Val | Glu | Val | Asp | Gly | Arg | Thr | Ile | Gly | Thr | Gly | Lys |
| | | | 260 | | | | | 265 | | | | | 270 | | |
| CCG | GGC | CCC | ATT | ACG | ACA | AAA | ATA | GCT | GAG | CTG | TAC | TCA | AAC | GTC | GTG |
| Pro | Gly | Pro | Ile | Thr | Thr | Lys | Ile | Ala | Glu | Leu | Tyr | Ser | Asn | Val | Val |
| | | 275 | | | | | 280 | | | | | 285 | | | |
| AGA | GGC | AAA | GTA | GAG | AAA | TAC | TTA | AAT | TGG | ATC | ACT | CCT | GTG | TAT | TAG |
| Arg | Gly | Lys | Val | Glu | Lys | Tyr | Leu | Asn | Trp | Ile | Thr | Pro | Val | Tyr | End |
| | 290 | | | | | 295 | | | | | 300 | | | | |

( 2 ) INFORMATION FOR SEQ ID NO:25:

( i ) SEQUENCE CHARACTERISTICS:
        ( A ) LENGTH: 414 AMINO ACIDS
        ( B ) TYPE: AMINO ACID
        ( D ) TOPOLOGY: LINEAR ( i i ) MOLECULE TYPE: PROTEIN ( x i ) SEQUENCE DESCRIPTION: SEQ ID NO:25:

| Met | Ile | Glu | Asp | Pro | Met | Asp | Trp | Ala | Phe | Pro | Arg | Ile | Lys | Arg | Leu |
|---|---|---|---|---|---|---|---|---|---|---|---|---|---|---|---|
| | | | | 5 | | | | | 10 | | | | | 15 | |
| Pro | Gln | Tyr | Val | Phe | Ser | Leu | Val | Asn | Glu | Leu | Lys | Tyr | Lys | Leu | Arg |
| | | | 20 | | | | | 25 | | | | | 30 | | |
| Arg | Glu | Gly | Glu | Asp | Val | Val | Asp | Leu | Gly | Met | Gly | Asn | Pro | Asn | Met |
| | | | 35 | | | | | 40 | | | | | 45 | | |
| Pro | Pro | Ala | Lys | His | Ile | Ile | Asp | Lys | Leu | Cys | Glu | Val | Ala | Gln | Lys |

| | | | | | 50 | | | | | 55 | | | | | 60 | | |
|---|---|---|---|---|---|---|---|---|---|---|---|---|---|---|---|---|---|
| Pro | Asn | Val | His | Gly | Tyr | Ser | Ala | Ser | Arg | Gly | Ile | Pro | Arg | Leu | Arg |
| 65 | | | | | 70 | | | | | 75 | | | | | 80 |
| Lys | Ala | Ile | Cys | Asn | Phe | Tyr | Glu | Glu | Arg | Tyr | Gly | Val | Lys | Leu | Asp |
| | | | | 85 | | | | | 90 | | | | | 95 | |
| Pro | Glu | Arg | Glu | Ala | Ile | Leu | Thr | Ile | Gly | Ala | Lys | Glu | Gly | Tyr | Ser |
| | | | 100 | | | | | 105 | | | | | 110 | | |
| His | Leu | Met | Leu | Ala | Met | Ile | Ser | Pro | Gly | Asp | Thr | Val | Ile | Val | Pro |
| | | | 115 | | | | 120 | | | | | 125 | | | |
| Asn | Pro | Thr | Tyr | Pro | Ile | His | Tyr | Tyr | Ala | Pro | Ile | Ile | Ala | Gly | Gly |
| | | 130 | | | | | 135 | | | | | 140 | | | |
| Glu | Val | His | Ser | Ile | Pro | Leu | Asn | Phe | Ser | Asp | Gln | Asp | His | Gln | |
| 145 | | | | | 150 | | | | | 155 | | | | | 160 |
| Glu | Glu | Phe | Leu | Arg | Arg | Leu | Tyr | Glu | Ile | Val | Lys | Thr | Ala | Met | Pro |
| | | | | 165 | | | | | 170 | | | | | 175 | |
| Lys | Pro | Lys | Ala | Val | Val | Ile | Ser | Phe | Pro | His | Asn | Pro | Thr | Thr | Ile |
| | | | 180 | | | | | 185 | | | | | 190 | | |
| Thr | Val | Glu | Lys | Asp | Phe | Phe | Lys | Glu | Ile | Val | Lys | Phe | Ala | Lys | Glu |
| | | 195 | | | | | 200 | | | | | 205 | | | |
| His | Gly | Leu | Trp | Ile | Ile | His | Asp | Phe | Ala | Tyr | Ala | Asp | Ile | Ala | Phe |
| | 210 | | | | | 215 | | | | | 220 | | | | |
| Asp | Gly | Tyr | Lys | Pro | Pro | Ser | Ile | Leu | Glu | Ile | Gly | Ala | Lys | Asp |
| 225 | | | | | 230 | | | | | 235 | | | | | 240 |
| Val | Ala | Val | Glu | Leu | Tyr | Ser | Met | Ser | Lys | Gly | Phe | Ser | Met | Ala | Gly |
| | | | | 245 | | | | | 250 | | | | | 255 | |
| Trp | Arg | Val | Ala | Phe | Val | Val | Gly | Asn | Glu | Ile | Leu | Ile | Lys | Asn | Leu |
| | | | 260 | | | | | 265 | | | | | 270 | | |
| Ala | His | Leu | Lys | Ser | Tyr | Leu | Asp | Tyr | Gly | Ile | Phe | Thr | Pro | Ile | Gln |
| | | 275 | | | | | 280 | | | | | 285 | | | |
| Val | Ala | Ser | Ile | Ile | Ala | Leu | Glu | Ser | Pro | Tyr | Glu | Ile | Val | Glu | Lys |
| | 290 | | | | | 295 | | | | | 300 | | | | |
| Thr | Ala | Lys | Val | Tyr | Gln | Lys | Arg | Arg | Asp | Val | Leu | Val | Glu | Gly | Leu |
| 305 | | | | | 310 | | | | | 315 | | | | | 320 |
| Asn | Arg | Leu | Gly | Trp | Lys | Val | Lys | Lys | Pro | Lys | Ala | Thr | Met | Phe | Val |
| | | | | 325 | | | | | 330 | | | | | 335 | |
| Trp | Ala | Lys | Ile | Pro | Glu | Trp | Ile | Asn | Met | Asn | Ser | Leu | Asp | Phe | Ser |
| | | | 340 | | | | | 345 | | | | | 350 | | |
| Leu | Phe | Leu | Leu | Lys | Glu | Ala | Lys | Ala | Val | Ser | Pro | Gly | Val | Gly |
| | | 355 | | | | | 360 | | | | | 365 | | | |
| Phe | Gly | Gln | Tyr | Gly | Glu | Gly | Tyr | Val | Arg | Phe | Ala | Leu | Val | Glu | Asn |
| | 370 | | | | | 375 | | | | | 380 | | | | |
| Glu | His | Arg | Ile | Arg | Gln | Ala | Ile | Arg | Gly | Ile | Arg | Lys | Ala | Phe | Arg |
| 385 | | | | | 390 | | | | | 395 | | | | | 400 |
| Lys | Leu | Gln | Lys | Glu | Arg | Lys | Leu | Glu | Pro | Glu | Arg | Ser | Ala |
| | | | | 405 | | | | | 410 | | | | 414 |

(2) INFORMATION FOR SEQ ID NO:26:

(i) SEQUENCE CHARACTERISTICS:
      (A) LENGTH: 373 AMINO ACIDS
      (B) TYPE: AMINO ACID
      (D) TOPOLOGY: LINEAR (ii) MOLECULE TYPE: PROTEIN (xi) SEQUENCE DESCRIPTION: SEQ ID NO:26:

```
Met  Asp  Arg  Leu  Glu  Lys  Val  Ser  Pro  Phe  Ile  Val  Met  Asp  Ile  Leu
               5                        10                       15

Ala  Gln  Ala  Gln  Lys  Tyr  Glu  Asp  Val  His  Met  Glu  Ile  Gly  Glu
               20                       25                  30

Pro  Asp  Leu  Glu  Pro  Ser  Pro  Lys  Val  Met  Glu  Ala  Leu  Glu  Arg  Ala
               35                       40                       45

Val  Lys  Glu  Lys  Thr  Phe  Phe  Tyr  Thr  Pro  Ala  Leu  Gly  Leu  Trp  Glu
          50                       55                       60

Leu  Arg  Glu  Arg  Ile  Ser  Glu  Phe  Tyr  Arg  Lys  Lys  Tyr  Ser  Val  Glu
65                            70                       75                       80

Val  Ser  Pro  Glu  Arg  Val  Ile  Val  Thr  Thr  Gly  Thr  Ser  Gly  Ala  Phe
                    85                       90                       95

Leu  Val  Ala  Tyr  Ala  Val  Thr  Leu  Asn  Ala  Gly  Glu  Lys  Ile  Ile  Leu
               100                      105                      110

Pro  Asp  Pro  Ser  Tyr  Pro  Cys  Tyr  Lys  Asn  Phe  Ala  Tyr  Leu  Leu  Asp
               115                      120                      125

Ala  Gln  Pro  Val  Phe  Val  Asn  Val  Asp  Lys  Glu  Thr  Asn  Tyr  Glu  Val
     130                      135                      140

Arg  Lys  Glu  Met  Ile  Glu  Asp  Ile  Asp  Ala  Lys  Ala  Leu  His  Ile  Ser
145                      150                      155                      160

Ser  Pro  Gln  Asn  Pro  Thr  Gly  Thr  Leu  Tyr  Ser  Pro  Glu  Thr  Leu  Lys
                    165                      170                      175

Glu  Leu  Ala  Glu  Tyr  Cys  Glu  Glu  Lys  Gly  Met  Tyr  Phe  Ile  Ser  Asp
               180                      185                      190

Glu  Ile  Tyr  His  Gly  Leu  Val  Tyr  Glu  Gly  Arg  Glu  His  Thr  Ala  Leu
          195                      200                      205

Glu  Phe  Ser  Asp  Arg  Ala  Ile  Val  Ile  Asn  Gly  Phe  Ser  Lys  Tyr  Phe
     210                      215                      220

Cys  Met  Pro  Gly  Phe  Arg  Ile  Gly  Trp  Met  Ile  Val  Pro  Glu  Glu  Leu
225                      230                      235                      240

Val  Arg  Lys  Ala  Glu  Ile  Val  Ile  Gln  Asn  Val  Phe  Ile  Ser  Ala  Pro
               245                      250                      255

Thr  Leu  Ser  Gln  Tyr  Ala  Ala  Leu  Glu  Ala  Phe  Asp  Tyr  Glu  Tyr  Leu
               260                      265                      270

Glu  Lys  Val  Arg  Lys  Thr  Phe  Glu  Glu  Arg  Arg  Asn  Phe  Leu  Tyr  Gly
          275                      280                      285

Glu  Leu  Lys  Lys  Leu  Phe  Lys  Ile  Asp  Ala  Lys  Pro  Gln  Gly  Ala  Phe
     290                      295                      300

Tyr  Val  Trp  Ala  Asn  Ile  Ser  Asp  Tyr  Ser  Thr  Asp  Ser  Tyr  Glu  Phe
305                      310                      315                      320

Ala  Leu  Lys  Leu  Leu  Arg  Glu  Ala  Arg  Val  Ala  Val  Thr  Pro  Gly  Val
               325                      330                      335

Asp  Phe  Gly  Lys  Asn  Lys  Thr  Lys  Glu  Tyr  Ile  Arg  Phe  Ala  Tyr  Thr
               340                      345                      350

Arg  Lys  Ile  Glu  Glu  Leu  Lys  Glu  Gly  Val  Glu  Arg  Ile  Lys  Lys  Phe
          355                      360                      365

Leu  Glu  Lys  Leu  Ser
     370
```

( 2 ) INFORMATION FOR SEQ ID NO:27:

( i ) SEQUENCE CHARACTERISTICS:
        ( A ) LENGTH: 453 AMINO ACIDS
        ( B ) TYPE: AMINO ACID
        ( D ) TOPOLOGY: LINEAR ( i i ) MOLECULE TYPE: PROTEIN ( x i ) SEQUENCE DESCRIPTION: SEQ ID NO:27:

| Met | Trp | Glu | Leu | Asp | Pro | Lys | Thr | Leu | Glu | Lys | Trp | Asp | Lys | Glu | Tyr |
|---|---|---|---|---|---|---|---|---|---|---|---|---|---|---|---|
| | | | | 5 | | | | | 10 | | | | | 15 | |
| Phe | Trp | His | Pro | Phe | Thr | Gln | Met | Lys | Val | Tyr | Arg | Glu | Glu | Glu | Asn |
| | | | 20 | | | | | 25 | | | | | 30 | | |
| Leu | Ile | Phe | Glu | Arg | Gly | Glu | Gly | Val | Tyr | Leu | Trp | Asp | Ile | Tyr | Gly |
| | | | 35 | | | | 40 | | | | | 45 | | | |
| Arg | Lys | Tyr | Ile | Asp | Ala | Ile | Ser | Ser | Leu | Trp | Cys | Asn | Val | His | Gly |
| | | 50 | | | | | 55 | | | | | 60 | | | |
| His | Asn | His | Pro | Lys | Leu | Asn | Asn | Ala | Val | Met | Lys | Gln | Leu | Cys | Lys |
| 65 | | | | | 70 | | | | | 75 | | | | | 80 |
| Val | Ala | His | Thr | Thr | Thr | Leu | Gly | Ser | Ser | Asn | Val | Pro | Ala | Ile | Leu |
| | | | | 85 | | | | | 90 | | | | | 95 | |
| Leu | Ala | Lys | Lys | Leu | Val | Glu | Ile | Ser | Pro | Glu | Gly | Leu | Asn | Lys | Val |
| | | | 100 | | | | | 105 | | | | | 110 | | |
| Phe | Tyr | Ser | Glu | Asp | Gly | Ala | Glu | Ala | Val | Glu | Ile | Ala | Ile | Lys | Met |
| | | | 115 | | | | | 120 | | | | | 125 | | |
| Ala | Tyr | His | Tyr | Trp | Lys | Asn | Lys | Gly | Val | Lys | Gly | Lys | Asn | Val | Phe |
| | | 130 | | | | | 135 | | | | | 140 | | | |
| Ile | Thr | Leu | Ser | Glu | Ala | Tyr | His | Gly | Asp | Thr | Val | Gly | Ala | Val | Ser |
| 145 | | | | | 150 | | | | | 155 | | | | | 160 |
| Val | Gly | Gly | Ile | Glu | Leu | Phe | His | Gly | Thr | Tyr | Lys | Asp | Leu | Leu | Phe |
| | | | | 165 | | | | | 170 | | | | | 175 | |
| Lys | Thr | Ile | Lys | Leu | Pro | Ser | Pro | Tyr | Leu | Tyr | Cys | Lys | Glu | Lys | Tyr |
| | | | 180 | | | | | 185 | | | | | 190 | | |
| Gly | Glu | Leu | Cys | Pro | Glu | Cys | Thr | Ala | Asp | Leu | Leu | Lys | Gln | Leu | Glu |
| | | | 195 | | | | | 200 | | | | | 205 | | |
| Asp | Ile | Leu | Lys | Ser | Arg | Glu | Asp | Ile | Val | Ala | Val | Ile | Met | Glu | Ala |
| | | 210 | | | | | 215 | | | | | 220 | | | |
| Gly | Ile | Gln | Ala | Ala | Ala | Gly | Met | Leu | Pro | Phe | Pro | Pro | Gly | Phe | Leu |
| 225 | | | | | 230 | | | | | 235 | | | | | 240 |
| Lys | Gly | Val | Arg | Glu | Leu | Thr | Lys | Lys | Tyr | Asp | Thr | Leu | Met | Ile | Val |
| | | | | 245 | | | | | 250 | | | | | 255 | |
| Asp | Glu | Val | Ala | Thr | Gly | Phe | Gly | Arg | Thr | Gly | Thr | Met | Phe | Tyr | Cys |
| | | | 260 | | | | | 265 | | | | | 270 | | |
| Glu | Gln | Glu | Gly | Val | Ser | Pro | Asp | Phe | Met | Cys | Leu | Gly | Lys | Gly | Ile |
| | | | 275 | | | | | 280 | | | | | 285 | | |
| Thr | Gly | Gly | Tyr | Leu | Pro | Leu | Ala | Ala | Thr | Leu | Thr | Thr | Asp | Glu | Val |
| | | 290 | | | | | 295 | | | | | 300 | | | |
| Phe | Asn | Ala | Phe | Leu | Gly | Glu | Phe | Gly | Glu | Ala | Lys | His | Phe | Tyr | His |
| 305 | | | | | 310 | | | | | 315 | | | | | 320 |
| Gly | His | Thr | Tyr | Thr | Gly | Asn | Asn | Leu | Ala | Cys | Ser | Val | Ala | Leu | Ala |
| | | | | 325 | | | | | 330 | | | | | 335 | |
| Asn | Leu | Glu | Val | Phe | Glu | Glu | Glu | Arg | Thr | Leu | Glu | Lys | Leu | Gln | Pro |
| | | | 340 | | | | | 345 | | | | | 350 | | |
| Lys | Ile | Lys | Leu | Leu | Lys | Glu | Arg | Leu | Gln | Glu | Phe | Trp | Glu | Leu | Lys |
| | | | 355 | | | | | 360 | | | | | 365 | | |
| His | Val | Gly | Asp | Val | Arg | Gln | Leu | Gly | Phe | Met | Ala | Gly | Ile | Glu | Leu |
| | | 370 | | | | | 375 | | | | | 380 | | | |
| Val | Lys | Asp | Lys | Glu | Lys | Gly | Glu | Pro | Phe | Pro | Tyr | Gly | Glu | Arg | Thr |
| 385 | | | | | 390 | | | | | 395 | | | | | 400 |
| Gly | Phe | Lys | Val | Ala | Tyr | Lys | Cys | Arg | Glu | Lys | Gly | Val | Phe | Leu | Arg |

|     |     |     |     | 405 |     |     |     | 410 |     |     |     | 415 |     |     |
| --- | --- | --- | --- | --- | --- | --- | --- | --- | --- | --- | --- | --- | --- | --- |
| Pro | Leu | Gly | Asp<br>420 | Val | Met | Val | Leu | Met<br>425 | Met | Pro | Leu | Val<br>430 | Ile | Glu | Glu |
| Asp | Glu | Met<br>435 | Asn | Tyr | Val | Ile | Asp<br>440 | Thr | Leu | Lys | Trp | Ala<br>445 | Ile | Lys | Glu |
| Leu | Glu | Lys | Glu | Val<br>450 | | | | | | | | | | | |

(2) INFORMATION FOR SEQ ID NO:28:

(i) SEQUENCE CHARACTERISTICS:
        (A) LENGTH: 343 AMINO ACIDS
        (B) TYPE: AMINO ACID
        (D) TOPOLOGY: LINEAR (ii) MOLECULE TYPE: PROTEIN (xi) SEQUENCE DESCRIPTION: SEQ ID NO:28:

| Met | Thr | Tyr | Leu | Met<br>5 | Asn | Asn | Tyr | Ala | Arg<br>10 | Leu | Pro | Val | Lys | Phe<br>15 | Val |
| --- | --- | --- | --- | --- | --- | --- | --- | --- | --- | --- | --- | --- | --- | --- | --- |
| Arg | Gly | Lys | Gly<br>20 | Val | Tyr | Leu | Tyr | Asp<br>25 | Glu | Glu | Gly | Lys | Glu<br>30 | Tyr | Leu |
| Asp | Phe | Val<br>35 | Ser | Gly | Ile | Gly | Val<br>40 | Asn | Ser | Leu | Gly | His<br>45 | Ala | Tyr | Pro |
| Lys | Leu<br>50 | Thr | Glu | Ala | Leu | Lys<br>55 | Glu | Gln | Val | Glu | Lys<br>60 | Leu | Leu | His | Val |
| Ser<br>65 | Asn | Leu | Tyr | Glu | Asn<br>70 | Pro | Trp | Gln | Glu | Glu<br>75 | Leu | Ala | His | Lys | Leu<br>80 |
| Val | Lys | His | Phe | Trp<br>85 | Thr | Glu | Gly | Lys | Val<br>90 | Phe | Phe | Ala | Asn | Ser<br>95 | Gly |
| Thr | Glu | Ser | Val<br>100 | Glu | Ala | Ala | Ile | Lys<br>105 | Leu | Ala | Arg | Lys | Tyr<br>110 | Trp | Arg |
| Asp | Lys | Gly<br>115 | Lys | Asn | Lys | Trp | Lys<br>120 | Phe | Ile | Ser | Phe | Glu<br>125 | Asn | Ser | Phe |
| His | Gly | Arg<br>130 | Thr | Tyr | Gly | Ser<br>135 | Leu | Ser | Ala | Thr | Gly<br>140 | Gln | Pro | Lys | Phe |
| His<br>145 | Lys | Gly | Phe | Glu | Pro<br>150 | Leu | Val | Pro | Gly | Phe<br>155 | Ser | Tyr | Ala | Lys | Leu<br>160 |
| Asn | Asp | Ile | Asp | Ser<br>165 | Val | Tyr | Lys | Leu | Leu<br>170 | Asp | Glu | Glu | Thr | Ala<br>175 | Gly |
| Ile | Ile | Ile | Glu<br>180 | Val | Ile | Gln | Gly<br>185 | Glu | Gly | Gly | Val | Asn<br>190 | Glu | Ala | Ser |
| Glu | Asp | Phe<br>195 | Leu | Ser | Lys | Leu | Gln<br>200 | Glu | Ile | Cys | Lys | Glu<br>205 | Lys | Asp | Val |
| Leu | Leu<br>210 | Ile | Ile | Asp | Glu | Val<br>215 | Gln | Thr | Gly | Ile | Gly<br>220 | Arg | Thr | Gly | Glu |
| Phe<br>225 | Tyr | Ala | Tyr | Gln | His<br>230 | Phe | Asn | Leu | Lys | Pro<br>235 | Asp | Val | Ile | Ala | Leu<br>240 |
| Ala | Lys | Gly | Leu | Gly<br>245 | Gly | Gly | Val | Pro | Ile<br>250 | Gly | Ala | Ile | Leu | Ala<br>255 | Arg |
| Glu | Glu | Val | Ala<br>260 | Gln | Ser | Phe | Thr | Pro<br>265 | Gly | Ser | His | Gly | Ser<br>270 | Thr | Phe |
| Gly | Gly | Asn<br>275 | Pro | Leu | Ala | Cys | Arg<br>280 | Ala | Gly | Thr | Val | Val<br>285 | Val | Asp | Glu |
| Val | Glu<br>290 | Lys | Leu | Leu | Pro | His<br>295 | Val | Arg | Glu | Val | Gly<br>300 | Asn | Tyr | Phe | Lys |

```
Glu  Lys  Leu  Lys  Glu  Leu  Gly  Lys  Gly  Lys  Val  Lys  Gly  Arg  Gly  Leu
305                      310                     315                     320

Met  Leu  Gly  Leu  Glu  Leu  Glu  Arg  Glu  Cys  Lys  Asp  Tyr  Val  Leu  Lys
                         325                     330                     335

Ala  Leu  Glu  Arg  Asp  Phe  Ser
                    340
```

( 2 ) INFORMATION FOR SEQ ID NO:29:

( i ) SEQUENCE CHARACTERISTICS:
        ( A ) LENGTH: 398 AMINO ACIDS
        ( B ) TYPE: AMINO ACID
        ( D ) TOPOLOGY: LINEAR ( i i ) MOLECULE TYPE: PROTEIN ( x i ) SEQUENCE DESCRIPTION: SEQ ID NO:29:

```
Met  Arg  Lys  Leu  Ala  Glu  Arg  Ala  Gln  Lys  Leu  Ser  Pro  Ser  Pro  Thr
                      5                      10                      15

Leu  Ser  Val  Asp  Thr  Lys  Ala  Lys  Glu  Leu  Leu  Arg  Gln  Gly  Glu  Arg
                     20                      25                      30

Val  Ile  Asn  Phe  Gly  Ala  Gly  Glu  Pro  Asp  Phe  Asp  Thr  Pro  Glu  His
                35                      40                      45

Ile  Lys  Glu  Ala  Ala  Lys  Arg  Ala  Leu  Asp  Gln  Gly  Phe  Thr  Lys  Tyr
          50                      55                      60

Thr  Pro  Val  Ala  Gly  Ile  Leu  Pro  Leu  Arg  Glu  Ala  Ile  Cys  Glu  Lys
65                       70                      75                       80

Leu  Tyr  Arg  Asp  Asn  Gln  Leu  Glu  Tyr  Ser  Pro  Asn  Glu  Ile  Val  Val
                    85                      90                       95

Ser  Cys  Gly  Ala  Lys  His  Ser  Ile  Phe  Asn  Ala  Leu  Gln  Val  Leu  Leu
               100                     105                     110

Asp  Pro  Gly  Asp  Glu  Val  Ile  Ile  Pro  Val  Pro  Tyr  Trp  Thr  Ser  Tyr
               115                     120                     125

Pro  Glu  Gln  Val  Lys  Leu  Ala  Gly  Gly  Val  Pro  Val  Phe  Val  Pro  Thr
          130                     135                     140

Ser  Pro  Glu  Asn  Asp  Phe  Lys  Leu  Arg  Pro  Glu  Asp  Leu  Arg  Ala  Ala
145                      150                     155                      160

Val  Thr  Pro  Arg  Thr  Arg  Leu  Leu  Ile  Leu  Asn  Ser  Pro  Ala  Asn  Pro
               165                     170                     175

Thr  Gly  Thr  Val  Tyr  Arg  Arg  Glu  Glu  Leu  Ile  Gly  Leu  Ala  Glu  Val
               180                     185                     190

Ala  Leu  Glu  Ala  Asp  Leu  Trp  Ile  Leu  Ser  Asp  Glu  Ile  Tyr  Glu  Lys
          195                     200                     205

Leu  Ile  Tyr  Asp  Gly  Met  Glu  His  Val  Ser  Ile  Ala  Ala  Leu  Asp  Pro
     210                     215                     220

Glu  Val  Lys  Lys  Arg  Thr  Ile  Val  Val  Asn  Gly  Val  Ser  Lys  Ala  Tyr
225                      230                     235                      240

Ala  Met  Thr  Gly  Trp  Arg  Ile  Gly  Tyr  Ala  Ala  Ala  Pro  Arg  Pro  Ile
               245                     250                     255

Ala  Gln  Ala  Met  Thr  Asn  Leu  Gln  Ser  His  Ser  Thr  Ser  Asn  Pro  Thr
               260                     265                     270

Ser  Val  Ala  Gln  Ala  Ala  Ala  Leu  Ala  Ala  Leu  Lys  Gly  Pro  Gln  Glu
          275                     280                     285

Pro  Val  Glu  Asn  Met  Arg  Arg  Ala  Phe  Gln  Lys  Arg  Arg  Asp  Phe  Ile
          290                     295                     300

Trp  Gln  Tyr  Leu  Asn  Ser  Leu  Pro  Gly  Val  Arg  Cys  Pro  Lys  Pro  Leu
305                      310                     315                      320
```

```
Gly  Ala  Phe  Tyr  Val  Phe  Pro  Glu  Val  Glu  Arg  Ala  Phe  Gly  Pro  Pro
                    325                 330                      335

Ser  Lys  Arg  Thr  Gly  Asn  Thr  Thr  Ala  Ser  Asp  Leu  Ala  Leu  Phe  Leu
               340                 345                      350

Leu  Glu  Glu  Ile  Lys  Val  Ala  Thr  Val  Ala  Gly  Ala  Ala  Phe  Gly  Asp
          355                      360                      365

Asp  Arg  Tyr  Leu  Arg  Phe  Ser  Tyr  Ala  Leu  Arg  Leu  Glu  Asp  Ile  Glu
     370                 375                      380

Glu  Gly  Met  Gln  Arg  Phe  Lys  Glu  Leu  Ile  Glu  Ala  Ala  Leu
385                      390                 395
```

( 2 ) INFORMATION FOR SEQ ID NO:30:

( i ) SEQUENCE CHARACTERISTICS:
        ( A ) LENGTH: 592 AMINO ACIDS
        ( B ) TYPE: AMINO ACID
        ( D ) TOPOLOGY: LINEAR ( i i ) MOLECULE TYPE: PROTEIN ( x i ) SEQUENCE DESCRIPTION: SEQ ID NO:30:

```
Met  Cys  Gly  Ile  Val  Gly  Tyr  Val  Gly  Arg  Asp  Leu  Ala  Leu  Pro  Ile
                    5                    10                       15

Val  Leu  Gly  Ala  Leu  Glu  Arg  Leu  Glu  Tyr  Arg  Gly  Tyr  Asp  Ser  Ala
               20                      25                       30

Gly  Val  Ala  Leu  Ile  Glu  Asp  Gly  Lys  Leu  Ile  Val  Glu  Lys  Lys  Lys
               35                      40                       45

Gly  Lys  Ile  Arg  Glu  Leu  Val  Lys  Ala  Leu  Trp  Gly  Lys  Asp  Tyr  Lys
     50                      55                       60

Ala  Lys  Thr  Gly  Ile  Gly  His  Thr  Arg  Trp  Ala  Thr  His  Gly  Lys  Pro
65                           70                       75                  80

Thr  Asp  Glu  Asn  Ala  His  Pro  His  Thr  Asp  Glu  Lys  Gly  Glu  Phe  Ala
                    85                      90                       95

Val  Val  His  Asn  Gly  Ile  Ile  Glu  Asn  Tyr  Leu  Glu  Leu  Lys  Glu  Glu
                    100                     105                      110

Leu  Lys  Lys  Glu  Gly  Val  Lys  Phe  Arg  Ser  Glu  Thr  Asp  Thr  Glu  Val
          115                     120                      125

Ile  Ala  His  Leu  Ile  Ala  Lys  Asn  Tyr  Arg  Gly  Asp  Leu  Leu  Glu  Ala
          130                     135                      140

Val  Leu  Lys  Thr  Val  Lys  Lys  Leu  Lys  Gly  Ala  Phe  Ala  Phe  Ala  Val
145                      150                     155                      160

Ile  Thr  Val  His  Glu  Pro  Asn  Arg  Leu  Ile  Gly  Val  Lys  Gln  Gly  Ser
                    165                     170                      175

Pro  Leu  Ile  Val  Gly  Leu  Gly  Glu  Gly  Glu  Asn  Phe  Leu  Ala  Ser  Asp
               180                     185                      190

Ile  Pro  Ala  Ile  Leu  Pro  Tyr  Thr  Lys  Lys  Ile  Ile  Val  Leu  Asp  Asp
          195                     200                      205

Gly  Glu  Ile  Ala  Asp  Leu  Thr  Pro  Asp  Thr  Val  Asn  Ile  Tyr  Asn  Phe
     210                     215                      220

Glu  Gly  Glu  Pro  Val  Ser  Lys  Glu  Val  Met  Ile  Thr  Pro  Trp  Asp  Leu
225                      230                     235                      240

Val  Ser  Ala  Glu  Lys  Gly  Gly  Phe  Lys  His  Phe  Met  Leu  Lys  Glu  Ile
                    245                     250                      255

Tyr  Glu  Gln  Pro  Lys  Ala  Ile  Asn  Asp  Thr  Leu  Lys  Gly  Phe  Leu  Ser
               260                     265                      270

Thr  Glu  Asp  Ala  Ile  Pro  Phe  Lys  Leu  Lys  Asp  Phe  Arg  Arg  Val  Leu
```

|   |   |   | 275 |   |   |   | 280 |   |   |   | 285 |   |   |
|---|---|---|---|---|---|---|---|---|---|---|---|---|---|
| Ile | Ile<br>290 | Ala | Cys | Gly | Thr | Ser<br>295 | Tyr | His | Ala | Gly | Phe<br>300 | Val | Gly | Lys | Tyr |
| Trp<br>305 | Ile | Glu | Arg | Phe | Ala<br>310 | Gly | Val | Pro | Thr | Glu<br>315 | Val | Ile | Tyr | Ala | Ser<br>320 |
| Glu | Phe | Arg | Tyr | Ala<br>325 | Asp | Val | Pro | Val | Ser<br>330 | Asp | Lys | Asp | Ile | Val<br>335 | Ile |
| Gly | Ile | Ser | Gln<br>340 | Ser | Gly | Glu | Thr | Ala<br>345 | Asp | Thr | Lys | Phe | Ala<br>350 | Leu | Gln |
| Ser | Ala | Lys<br>355 | Glu | Lys | Gly | Ala | Phe<br>360 | Thr | Val | Gly | Leu | Val<br>365 | Asn | Val | Val |
| Gly | Ser<br>370 | Ala | Ile | Asp | Arg | Glu<br>375 | Ser | Asp | Phe | Ser | Leu<br>380 | His | Thr | His | Ala |
| Gly<br>385 | Pro | Glu | Ile | Gly | Val<br>390 | Ala | Ala | Thr | Lys | Thr<br>395 | Phe | Thr | Ala | Gln | Phe<br>400 |
| Thr | Ala | Leu | Tyr | Ala<br>405 | Leu | Ser | Val | Arg | Glu<br>410 | Ser | Glu | Glu | Arg | Glu<br>415 | Asn |
| Leu | Ile | Arg | Leu<br>420 | Leu | Glu | Lys | Val | Pro<br>425 | Ser | Leu | Val | Glu | Gln<br>430 | Thr | Leu |
| Asn | Thr | Ala<br>435 | Glu | Glu | Val | Glu | Lys<br>440 | Val | Ala | Glu | Lys | Tyr<br>445 | Met | Lys | Lys |
| Lys | Asn<br>450 | Met | Leu | Tyr | Leu | Gly<br>455 | Arg | Tyr | Leu | Asn | Tyr<br>460 | Pro | Ile | Ala | Leu |
| Glu<br>465 | Gly | Ala | Leu | Lys | Leu<br>470 | Lys | Glu | Ile | Ser | Tyr<br>475 | Ile | His | Ala | Glu | Gly<br>480 |
| Tyr | Pro | Ala | Gly | Glu<br>485 | Met | Lys | His | Gly | Pro<br>490 | Ile | Ala | Leu | Ile | Asp<br>495 | Glu |
| Asn | Met | Pro | Val<br>500 | Val | Val | Ile | Ala | Pro<br>505 | Lys | Asp | Arg | Val | Tyr<br>510 | Glu | Lys |
| Ile | Leu | Ser<br>515 | Asn | Val | Glu | Glu | Val<br>520 | Leu | Ala | Arg | Lys | Gly<br>525 | Arg | Val | Ile |
| Ser | Val<br>530 | Gly | Phe | Lys | Gly | Asp<br>535 | Glu | Thr | Leu | Lys | Ser<br>540 | Lys | Ser | Glu | Ser |
| Val<br>545 | Met | Glu | Ile | Pro | Lys<br>550 | Ala | Glu | Glu | Pro | Ile<br>555 | Thr | Pro | Phe | Leu | Thr<br>560 |
| Val | Ile | Pro | Leu | Gln<br>565 | Leu | Phe | Ala | Tyr | Phe<br>570 | Ile | Ala | Ser | Lys | Leu<br>575 | Gly |
| Leu | Asp | Val | Asp<br>580 | Gln | Pro | Arg | Asn | Leu<br>585 | Ala | Lys | Thr | Val | Thr<br>590 | Val | Glu |

( 2 ) INFORMATION FOR SEQ ID NO:31:

( i ) SEQUENCE CHARACTERISTICS:
        ( A ) LENGTH: 354 AMINO ACIDS
        ( B ) TYPE: AMINO ACID
        ( D ) TOPOLOGY: LINEAR ( i i ) MOLECULE TYPE: PROTEIN ( x i ) SEQUENCE DESCRIPTION: SEQ ID NO:31:

| Met | Ile | Pro | Gln | Arg<br>5 | Ile | Lys | Glu | Leu | Glu<br>10 | Ala | Tyr | Lys | Thr | Glu<br>15 | Val |
|---|---|---|---|---|---|---|---|---|---|---|---|---|---|---|---|
| Thr | Pro | Ala | Ser<br>20 | Val | Arg | Leu | Ser | Ser<br>25 | Asn | Glu | Phe | Pro | Tyr<br>30 | Asp | Phe |
| Pro | Glu | Glu<br>35 | Ile | Lys | Gln | Arg | Ala<br>40 | Leu | Glu | Glu | Leu | Lys<br>45 | Lys | Val | Pro |

```
Leu  Asn  Lys  Tyr  Pro  Asp  Pro  Glu  Ala  Lys  Glu  Leu  Lys  Ala  Val  Leu
      50             55                  60

Ala  Asp  Phe  Phe  Gly  Val  Lys  Glu  Glu  Asn  Leu  Val  Leu  Gly  Asn  Gly
 65             70                  75                                      80

Ser  Asp  Glu  Leu  Ile  Tyr  Tyr  Leu  Ser  Ile  Ala  Ile  Gly  Glu  Leu  Tyr
                85                            90                       95

Ile  Pro  Val  Tyr  Ile  Pro  Val  Pro  Thr  Phe  Pro  Met  Tyr  Glu  Ile  Ser
               100                 105                      110

Ala  Lys  Val  Leu  Gly  Arg  Pro  Leu  Val  Lys  Val  Gln  Leu  Asp  Glu  Asn
               115                 120                      125

Phe  Asp  Ile  Asp  Leu  Glu  Arg  Ser  Ile  Glu  Leu  Ile  Glu  Lys  Glu  Lys
      130                 135                      140

Pro  Val  Leu  Gly  Tyr  Phe  Ala  Tyr  Pro  Asn  Asn  Pro  Thr  Gly  Asn  Leu
145                      150                 155                           160

Phe  Ser  Arg  Gly  Lys  Ile  Glu  Glu  Ile  Arg  Asn  Arg  Gly  Val  Phe  Cys
               165                      170                           175

Val  Ile  Asp  Glu  Ala  Tyr  Tyr  His  Tyr  Ser  Gly  Glu  Thr  Phe  Leu  Glu
               180                 185                      190

Asp  Ala  Leu  Lys  Arg  Glu  Asp  Thr  Val  Val  Leu  Arg  Thr  Leu  Ser  Lys
               195                 200                      205

Ile  Gly  Met  Ala  Ser  Leu  Arg  Val  Gly  Ile  Leu  Ile  Gly  Lys  Gly  Glu
      210                 215                      220

Ile  Val  Ser  Glu  Ile  Asn  Lys  Val  Arg  Leu  Pro  Phe  Asn  Val  Thr  Tyr
225                      230                 235                           240

Pro  Ser  Gln  Val  Met  Ala  Lys  Val  Leu  Leu  Thr  Glu  Gly  Arg  Glu  Phe
               245                      250                           255

Leu  Met  Glu  Lys  Ile  Gln  Glu  Val  Val  Thr  Glu  Arg  Glu  Arg  Met  Tyr
               260                      265                      270

Asp  Glu  Met  Lys  Lys  Ile  Glu  Gly  Val  Glu  Val  Phe  Pro  Ser  Lys  Ala
               275                 280                      285

Asn  Phe  Leu  Leu  Phe  Arg  Thr  Pro  Tyr  Pro  Ala  His  Glu  Val  Tyr  Gln
      290                 295                      300

Glu  Leu  Leu  Lys  Arg  Asp  Val  Leu  Val  Arg  Asn  Val  Ser  Tyr  Met  Glu
305                      310                 315                           320

Gly  Leu  Gln  Lys  Cys  Leu  Arg  Val  Ser  Val  Gly  Lys  Pro  Glu  Glu  Asn
               325                      330                      335

Asn  Lys  Phe  Leu  Glu  Ala  Leu  Glu  Glu  Ser  Ile  Lys  Ser  Leu  Ser  Ser
               340                 345                      350

Ser  Leu
```

( 2 ) INFORMATION FOR SEQ ID NO:32:

( i ) SEQUENCE CHARACTERISTICS:
        ( A ) LENGTH: 303 AMINO ACIDS
        ( B ) TYPE: AMINO ACID
        ( D ) TOPOLOGY: LINEAR ( i i ) MOLECULE TYPE: PROTEIN ( x i ) SEQUENCE DESCRIPTION: SEQ ID NO:32:

```
Met  Lys  Pro  Tyr  Ala  Lys  Tyr  Ile  Trp  Leu  Asp  Gly  Arg  Ile  Leu  Lys
                5                       10                            15

Trp  Glu  Asp  Ala  Lys  Ile  His  Val  Leu  Thr  His  Ala  Leu  His  Tyr  Gly
                20                      25                            30

Thr  Ser  Ile  Phe  Glu  Gly  Ile  Arg  Gly  Tyr  Trp  Asn  Gly  Asp  Asn  Leu
           35                      40                            45
```

-continued

| | | | | | | | | | | | | | |
|---|---|---|---|---|---|---|---|---|---|---|---|---|---|
| Leu | Val 50 | Phe | Arg | Leu | Glu 55 | Glu | His | Ile | Asp | Arg | Met 60 | Tyr | Arg | Ser | Ala |
| Lys 65 | Ile | Leu | Gly | Ile | Asn 70 | Ile | Pro | Tyr | Thr | Arg 75 | Glu | Glu | Val | Arg | Gln 80 |
| Ala | Val | Leu | Glu | Thr 85 | Ile | Lys | Ala | Asn | Asn 90 | Phe | Arg | Glu | Asp | Val 95 | Tyr |
| Ile | Arg | Pro | Val 100 | Ala | Phe | Val | Ala | Ser 105 | Gln | Thr | Val | Thr | Leu 110 | Asp | Ile |
| Arg | Asn | Leu 115 | Glu | Val | Ser | Leu | Ala 120 | Val | Ile | Val | Phe | Pro 125 | Phe | Gly | Lys |
| Tyr | Leu 130 | Ser | Pro | Asn | Gly | Ile 135 | Lys | Ala | Thr | Ile | Val 140 | Ser | Trp | Arg | Arg |
| Val 145 | His | Asn | Thr | Met | Leu 150 | Pro | Val | Met | Ala | Lys 155 | Ile | Gly | Gly | Ile | Tyr 160 |
| Val | Asn | Ser | Val | Leu 165 | Ala | Leu | Val | Glu | Ala 170 | Arg | Ser | Arg | Gly | Phe 175 | Asp |
| Glu | Ala | Leu | Leu 180 | Met | Asp | Val | Asn | Gly 185 | Tyr | Val | Val | Glu | Gly 190 | Ser | Gly |
| Glu | Asn | Ile 195 | Phe | Ile | Val | Arg | Gly 200 | Gly | Arg | Leu | Phe | Thr 205 | Pro | Pro | Val |
| His | Glu 210 | Ser | Ile | Leu | Glu | Gly 215 | Ile | Thr | Arg | Asp | Thr 220 | Val | Ile | Lys | Leu |
| Ser 225 | Gly | Asp | Val | Gly | Leu 230 | Arg | Val | Glu | Glu | Lys 235 | Pro | Ile | Thr | Arg | Glu 240 |
| Glu | Val | Tyr | Thr | Ala 245 | Asp | Glu | Val | Phe | Leu 250 | Val | Gly | Thr | Ala | Ala 255 | Glu |
| Ile | Thr | Pro | Val 260 | Val | Glu | Val | Asp | Gly 265 | Arg | Thr | Ile | Gly | Thr 270 | Gly | Lys |
| Pro | Gly | Pro 275 | Ile | Thr | Thr | Lys | Ile 280 | Ala | Glu | Leu | Tyr | Ser 285 | Asn | Val | Val |
| Arg | Gly 290 | Lys | Val | Glu | Lys | Tyr 295 | Leu | Asn | Trp | Ile | Thr 300 | Pro | Val | Tyr | |